United States Patent
Wesley et al.

(10) Patent No.: US 9,693,799 B2
(45) Date of Patent: Jul. 4, 2017

(54) SYSTEM AND METHOD FOR ALIGNING HAIR FOLLICLE

(71) Applicant: PiloFocus, Inc., New York, NY (US)

(72) Inventors: Carlos K. Wesley, New York, NY (US); Trevor K. Lewis, Lehi, UT (US)

(73) Assignee: PiloFocus, Inc., New York, NY (US)

( * ) Notice: Subject to any disclaimer, the term of this patent is extended or adjusted under 35 U.S.C. 154(b) by 434 days.

(21) Appl. No.: 14/273,009

(22) Filed: May 8, 2014

(65) Prior Publication Data

US 2014/0243870 A1    Aug. 28, 2014

Related U.S. Application Data

(60) Provisional application No. 61/821,098, filed on May 8, 2013.

(51) Int. Cl.
  *A61B 17/34* (2006.01)
  *A45D 26/00* (2006.01)
  (Continued)

(52) U.S. Cl.
  CPC .............. *A61B 17/34* (2013.01); *A45D 26/00* (2013.01); *A61B 17/32002* (2013.01);
  (Continued)

(58) Field of Classification Search
  CPC .. A45D 26/00; A61B 34/20; A61B 17/32053; A61B 90/10; A61B 2090/101; A61B 90/11; A61B 17/3468; A61B 5/15146; A61B 5/15148; A61B 5/15149; A61B 5/15159; A61B 5/15161; A61B 5/15163; A61B 5/15171; A61B 5/15173;
  (Continued)

(56) References Cited

U.S. PATENT DOCUMENTS 4,476,864 A    10/1984 Tezel
4,763,669 A    8/1988 Jaeger
(Continued)

FOREIGN PATENT DOCUMENTS

EP    1642541 A1    4/2006
GB    2021467 A    12/1979
(Continued)

OTHER PUBLICATIONS

Office Action with English translation for related South Korean Application No. 10-2012-7009817, dated Dec. 14, 2015 (13 pages).
(Continued)

*Primary Examiner* — Jonathan Miles
(74) *Attorney, Agent, or Firm* — Craig Buschmann; Ryan L. Marshall; Brinks Gilson & Lione

(57) ABSTRACT

Systems and methods for aligning hair follicle are provided. The systems may include at least one piercing member. The piercing member may be configured to pivot about a pivot axis. The piercing member may be operable to translate along a chosen axis, wherein the chosen axis may intersect with the pivot axis. The translation of the piercing member in a first direction may enable the piercing member to pierce through an external surface of a skin, and translation of the piercing member in a second direction may enable the piercing member to retract out of the skin.

4 Claims, 39 Drawing Sheets

(51) Int. Cl.
  *A61B 17/32* (2006.01)
  *A61B 17/3205* (2006.01)
  *A61B 90/50* (2016.01)
  *A61F 2/10* (2006.01)
  *A61B 17/3209* (2006.01)
  *A61B 17/00* (2006.01)
  *A61B 90/00* (2016.01)

(52) U.S. Cl.
  CPC ......... *A61B 17/320016* (2013.01); *A61B 17/32053* (2013.01); *A61B 17/3468* (2013.01); *A61B 90/50* (2016.02); *A61B 17/32093* (2013.01); *A61B 2017/00752* (2013.01); *A61B 2017/32004* (2013.01); *A61B 2090/378* (2016.02); *A61B 2217/005* (2013.01); *A61F 2/10* (2013.01)

(58) Field of Classification Search
  CPC ............ A61B 17/34; A61B 17/3401; A61B 5/150412; A61B 5/150442; A61B 5/150374; A61B 5/150885; A61B 5/150893; A61B 5/150916
  See application file for complete search history.

(56) References Cited

U.S. PATENT DOCUMENTS

| | | |
|---|---|---|
| 5,133,360 A | 7/1992 | Spears |
| 5,133,722 A | 7/1992 | Avrahami et al. |
| 5,135,531 A | 8/1992 | Shiber |
| 5,368,014 A | 11/1994 | Anapliotis et al. |
| 5,391,166 A | 2/1995 | Eggers |
| 5,439,475 A | 8/1995 | Bennett |
| 5,445,615 A | 8/1995 | Yoon |
| 5,472,439 A | 12/1995 | Hurd |
| 5,478,351 A | 12/1995 | Meade et al. |
| 5,535,759 A | 7/1996 | Wilk |
| 5,601,601 A | 2/1997 | Tal et al. |
| 5,618,303 A | 4/1997 | Marlow et al. |
| 5,630,782 A | 5/1997 | Adair |
| 5,665,100 A | 9/1997 | Yoon |
| 5,676,678 A | 10/1997 | Schad |
| 5,676,680 A | 10/1997 | Lim |
| 5,782,851 A | 7/1998 | Rassman |
| 5,782,853 A | 7/1998 | Zeevi et al. |
| 5,788,651 A | 8/1998 | Weilandt |
| 5,792,163 A | 8/1998 | Hitzig |
| 5,817,120 A | 10/1998 | Rassman |
| 5,823,971 A | 10/1998 | Robinson et al. |
| 5,827,297 A | 10/1998 | Boudjema |
| 5,895,403 A | 4/1999 | Collinsworth |
| 5,922,000 A | 7/1999 | Chodorow |
| 5,984,936 A | 11/1999 | Mangubat et al. |
| 6,027,512 A | 2/2000 | Bridges |
| 6,059,719 A | 5/2000 | Yamamoto et al. |
| 6,352,503 B1 | 3/2002 | Matsui et al. |
| 6,419,627 B1 | 7/2002 | Nun |
| 6,500,170 B2 | 12/2002 | Palmer et al. |
| 6,544,259 B1 | 4/2003 | Tsaliovich |
| 6,572,625 B1 | 6/2003 | Rassman |
| 6,585,746 B2 | 7/2003 | Gildenberg |
| 6,620,158 B2 | 9/2003 | Ronci |
| 7,130,717 B2 | 10/2006 | Gildenberg |
| 7,156,856 B2 | 1/2007 | Feller |
| 7,261,721 B2 | 8/2007 | Feller |
| 7,329,252 B1 | 2/2008 | Yamazaki et al. |
| 7,517,321 B2 | 4/2009 | McCullough et al. |
| 7,621,933 B2 | 11/2009 | Bodduluri |
| 7,621,934 B2 | 11/2009 | Bodduluri |
| 7,627,157 B2 | 12/2009 | Qureshi |
| 7,727,164 B2 | 6/2010 | Cicenas et al. |
| 7,806,121 B2 | 10/2010 | Bodduluri |
| RE42,381 E | 5/2011 | Gildenberg |
| RE42,437 E | 6/2011 | Gildenberg |
| RE42,438 E | 6/2011 | Gildenberg |
| 7,962,192 B2 | 6/2011 | Bodduluri |
| 8,048,090 B2 | 11/2011 | Qureshi |
| 8,066,717 B2 | 11/2011 | DuBois |
| 8,104,480 B2 | 1/2012 | Bodduluri |
| 8,128,639 B2 | 3/2012 | Tippett |
| 8,133,237 B2 | 3/2012 | Oostman, Jr. |
| 8,133,247 B2 | 3/2012 | Bodduluri et al. |
| 8,317,804 B1 | 11/2012 | Rassman et al. |
| 8,454,627 B2 | 6/2013 | Bodduluri et al. |
| 8,690,894 B2 | 4/2014 | Bodduluri et al. |
| 8,998,931 B2 | 4/2015 | Wesley et al. |
| 2002/0042623 A1 | 4/2002 | Blatter et al. |
| 2002/0103500 A1 | 8/2002 | Gildenberg |
| 2003/0040706 A1 | 2/2003 | Kuracina et al. |
| 2003/0097143 A1 | 5/2003 | Mittelstaedt |
| 2003/0097144 A1 | 5/2003 | Lee |
| 2003/0120298 A1 | 6/2003 | Gildenberg |
| 2003/0212415 A1 | 11/2003 | Karasiuk |
| 2003/0233114 A1 | 12/2003 | Merboth |
| 2004/0049206 A1 | 3/2004 | Rassman |
| 2004/0092924 A1 | 5/2004 | Vasa |
| 2004/0097973 A1 | 5/2004 | Loshakove et al. |
| 2005/0049622 A1 | 3/2005 | Mittelstaeot |
| 2005/0177142 A1 | 8/2005 | Jay |
| 2005/0216035 A1 | 9/2005 | Kraus et al. |
| 2005/0267506 A1 | 12/2005 | Harris |
| 2006/0142741 A1 | 6/2006 | Jay |
| 2006/0161179 A1 | 7/2006 | Kachenmeister |
| 2006/0178677 A1 | 8/2006 | Brinson |
| 2006/0200040 A1 | 9/2006 | Weikel et al. |
| 2006/0259102 A1 | 11/2006 | Slatkine |
| 2007/0078466 A1 | 4/2007 | Bodduluri |
| 2007/0078473 A1 | 4/2007 | Bodduluri et al. |
| 2007/0106307 A1 | 5/2007 | Bodduluri |
| 2007/0122387 A1 | 5/2007 | Cochran |
| 2007/0128172 A1 | 6/2007 | Yoshizato |
| 2007/0156164 A1 | 7/2007 | Cole |
| 2007/0213741 A1 | 9/2007 | Cole |
| 2007/0255293 A1 | 11/2007 | Corre |
| 2007/0293884 A9 | 12/2007 | Cole |
| 2008/0033410 A1 | 2/2008 | Rastegar et al. |
| 2008/0033455 A1 | 2/2008 | Rassman |
| 2008/0051805 A1 | 2/2008 | Pinchuk |
| 2008/0051806 A1 | 2/2008 | Cole |
| 2008/0082114 A1* | 4/2008 | McKenna ......... A61B 17/0643 606/153 |
| 2008/0091225 A1 | 4/2008 | Cole et al. |
| 2008/0097458 A1 | 4/2008 | Donahoe et al. |
| 2008/0177287 A1 | 7/2008 | Rassman |
| 2008/0186496 A1 | 8/2008 | Leveque e |
| 2008/0200861 A1 | 8/2008 | Shalev et al. |
| 2008/0215039 A1 | 9/2008 | Slatkine et al. |
| 2008/0234697 A1 | 9/2008 | DuBois |
| 2008/0234698 A1 | 9/2008 | Oostman |
| 2009/0005765 A1 | 1/2009 | Oostman |
| 2009/0012536 A1 | 1/2009 | Rassman et al. |
| 2009/0052738 A1 | 2/2009 | Qureshi |
| 2009/0088776 A1 | 4/2009 | Harris |
| 2009/0192456 A1* | 7/2009 | Lee ............ A61B 5/1411 604/110 |
| 2009/0240261 A1 | 9/2009 | Drews |
| 2009/0306498 A1 | 12/2009 | Bodduluri |
| 2009/0306680 A1 | 12/2009 | Qureshi |
| 2010/0080415 A1 | 4/2010 | Qureshi |
| 2010/0080417 A1 | 4/2010 | Qureshi |
| 2010/0082042 A1 | 4/2010 | Drews |
| 2010/0125287 A1 | 5/2010 | Cole |
| 2010/0166719 A1 | 7/2010 | Yoshizato |
| 2010/0217236 A1 | 8/2010 | Gill |
| 2010/0262129 A1 | 10/2010 | Roy |
| 2011/0046639 A1 | 2/2011 | Giotis |
| 2011/0060321 A1 | 3/2011 | Chandler |
| 2011/0160746 A1 | 6/2011 | Umar |
| 2011/0178533 A1 | 7/2011 | Oostman |
| 2011/0224693 A1 | 9/2011 | Bodduluri |
| 2011/0245845 A1 | 10/2011 | Oostman |
| 2011/0319921 A1 | 12/2011 | Giotis |
| 2012/0010631 A1 | 1/2012 | DuBois |

(56) References Cited

U.S. PATENT DOCUMENTS

| | | |
|---|---|---|
| 2012/0039516 A1 | 2/2012 | Qureshi |
| 2012/0041430 A1 | 2/2012 | Anderson |
| 2012/0041451 A1 | 2/2012 | Bodduluri |
| 2012/0215231 A1 | 8/2012 | Wesley |
| 2013/0096600 A1 | 4/2013 | Wesley et al. |
| 2013/0190776 A1 | 7/2013 | Zhang et al. |
| 2013/0226213 A1 | 8/2013 | Kim et al. |
| 2013/0304090 A1 | 11/2013 | Oostman et al. |
| 2014/0236181 A1 | 8/2014 | Wesley et al. |
| 2014/0243870 A1 | 8/2014 | Wesley et al. |
| 2015/0012012 A1 | 1/2015 | Wesley et al. |
| 2015/0012013 A1 | 1/2015 | Wesley et al. |
| 2015/0223840 A1 | 8/2015 | Wesley et al. |

FOREIGN PATENT DOCUMENTS

| | | |
|---|---|---|
| JP | 59-114511 | 7/1984 |
| JP | 64-080335 | 3/1989 |
| JP | 03-086315 | 4/1991 |
| JP | 09-215656 | 8/1997 |
| JP | 2000-014631 A | 1/2000 |
| JP | 2000-037348 A | 2/2000 |
| JP | 2001-511393 A | 8/2001 |
| JP | 2008-502437 A | 1/2008 |
| JP | 2011-516169 A | 5/2011 |
| KR | 2007-0037577 A | 4/2007 |
| WO | WO 99/05997 A1 | 2/1999 |
| WO | WO 01/35125 A1 | 5/2001 |
| WO | WO 2005/109799 A2 | 11/2005 |
| WO | WO 2007/041267 A2 | 4/2007 |
| WO | WO 2007/087463 A2 | 8/2007 |
| WO | WO 2008/024954 A2 | 2/2008 |
| WO | WO 2008/027829 A2 | 3/2008 |
| WO | WO 2009/083741 A1 | 7/2009 |
| WO | WO 2009/123635 A1 | 10/2009 |
| WO | WO 2009/146068 A1 | 12/2009 |
| WO | WO 2010/039413 A1 | 4/2010 |
| WO | WO 2010/041089 A1 | 4/2010 |
| WO | WO 2010/057018 A2 | 5/2010 |
| WO | WO 2010/131270 A1 | 11/2010 |
| WO | WO 2011/035125 A1 | 3/2011 |
| WO | WO 2011/082130 A2 | 7/2011 |
| WO | WO 2011/123218 A1 | 10/2011 |
| WO | WO 2013/059349 A1 | 4/2013 |
| WO | WO 2014/182941 A1 | 11/2014 |

OTHER PUBLICATIONS

Final Office Action for related U.S. Appl. No. 13/496,905 with related technology, dated Nov. 28, 2014 (17 pages).

Patent Examination Report No. 1 for Australian Application No. 2014203223, dated Apr. 30, 2015 (3 pages).

Second Office Action for corresponding Chinese Application No. 201080052239.3, dated Nov. 19, 2014 (15 pages).

Invitation to Pay Additional Fees and, Where Applicable, Protest Fee for corresponding International Application No. PCT/US2014/037358, dated Sep. 4, 2014 (6 pages).

International Search Report and Written Opinion for corresponding International Application No. PCT/US2014/037358, dated Oct. 27, 2014 (15 pages).

Chinese Office Action (English Translation) for related Chinese Application No. 201080052239.3, entered Apr. 11, 2014 (9 pages).

International Preliminary Report on Patentability for International Application No. PCT/US2012/060653, dated Apr. 22, 2014 (8 pages).

Japanese Office Action (English Translation) for related Japanese Application No. 2012-529930, entered Apr. 15, 2014 (6 pages).

Notification of Reasons for Rejection with English translation for related Japanese Application No. 2014-537187, dated Jan. 5, 2016 (4 pages).

Office Action for related U.S. Appl. No. 14/273,058, dated Aug. 25, 2016 (37 pages).

Office Action for related U.S. Appl. No. 14/273,105, dated Sep. 16, 2016 (41 pages).

* cited by examiner

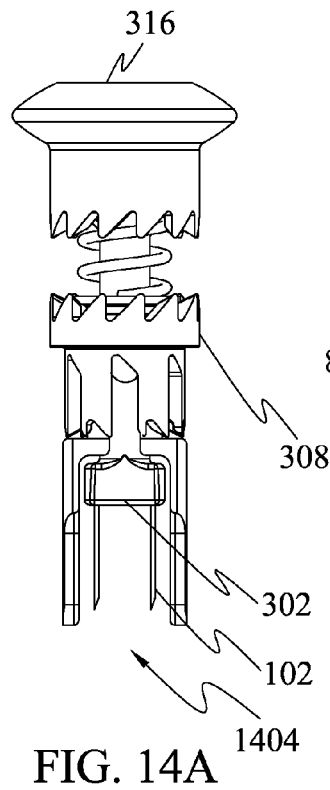
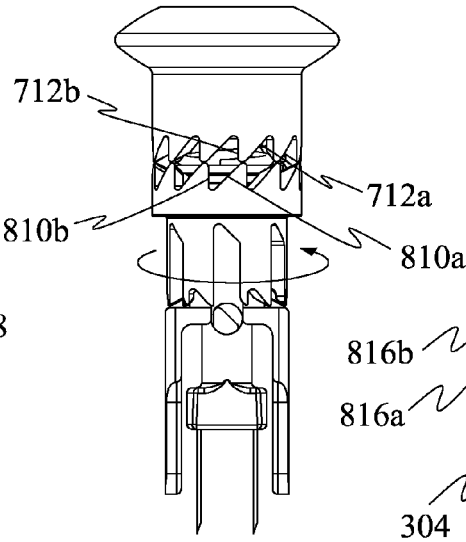
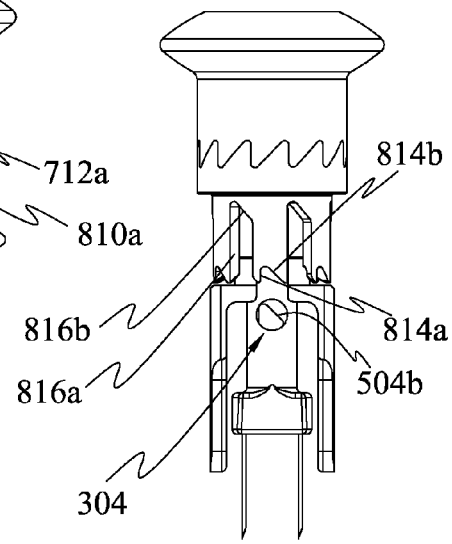
FIG. 14A  FIG. 14B  FIG. 14C
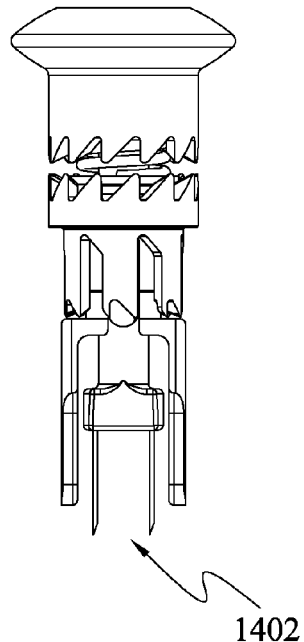
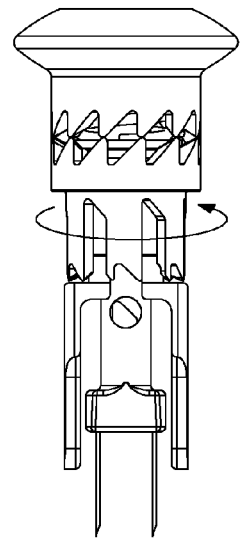
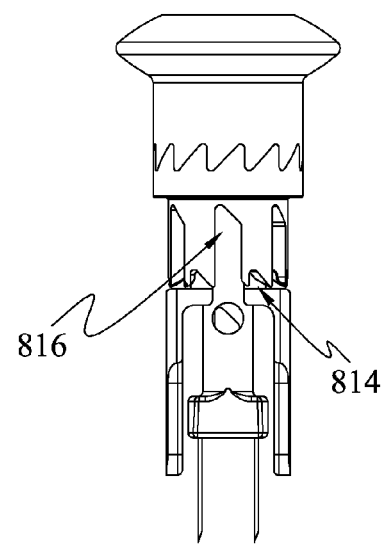
FIG. 14D  FIG. 14E  FIG. 14F

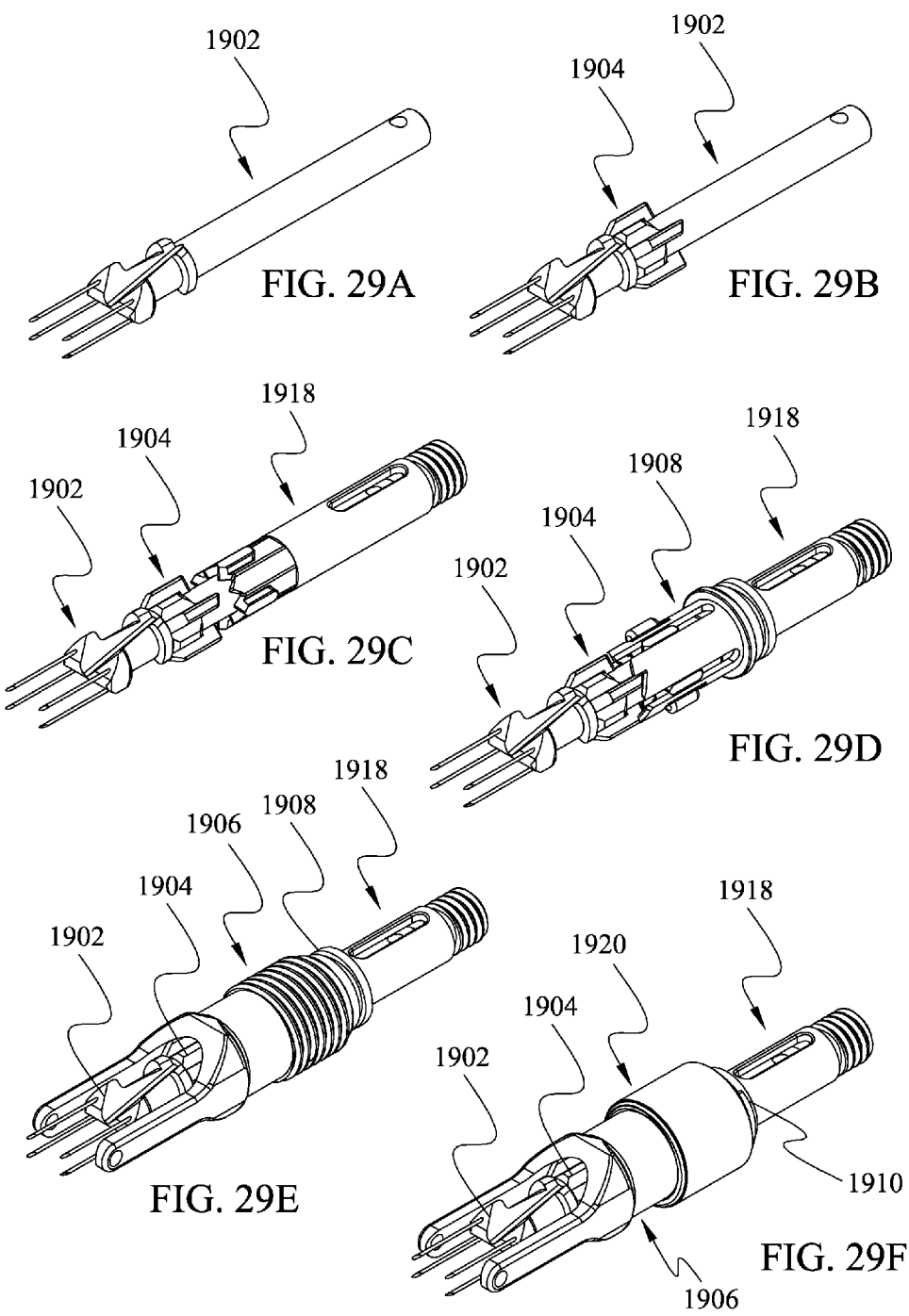

1

SYSTEM AND METHOD FOR ALIGNING HAIR FOLLICLE

CROSS-REFERENCE TO RELATED APPLICATIONS

This application claims the benefit of prior U.S. Provisional Patent Application No. 61/821,098 filed May 8, 2013.

The above-identified documents are incorporated herein by reference.

BACKGROUND

Technical Field

The present disclosure relates to technique for extracting a target hair follicle from a donor site. More particularly, but not exclusively, the present disclosure relates to altering alignment of the hair follicle to facilitate extraction.

Discussion of Related Art

Hair restoration may be carried out by extracting individual hair follicular units from the patient's donor area and transplanting them in the patient's recipient area, which may be a thinning area. Generally, the donor area is at the back and sides of the scalp.

Conventionally, a strip of tissues may be removed from the donor area. The strip may be then dissected into individual follicular units. The units may then be transplanted into the recipient area. It has been observed that application of this technique results in a linear scar formed at the donor area.

In another conventional technique, a hair follicle is extracted by punching a hole around the hair follicle, and then extracting the hair follicle. The hole is punched through the external surface of the skin. It has been observed that application of this technique may result in dotted scars formed at the donor area. Further, in this technique, the hair follicle may be transected, as the punch may not be aligned with the alignment of the hair follicle.

In light of the foregoing discussion, there may be a need to reduce scarring in the donor site, and reduce transection of hair follicle during extraction.

After the preparation of follicular unit grafts doctors make tiny holes in the patient's scalp called recipient area where grafts are placed. The positioning and arrangement of follicular units depends upon aesthetic qualities of a hair transplant, case-by-case basis, depending on the patients' history of hair loss and likelihood of future hair loss.

Francisco Jimenez, MD, Ander Izeta, PhD, and Enrique Poblet, MD. "Morphometric Analysis of the Human Scalp Hair Follicle: Practical Implications for the Hair Transplant Surgeon and Hair Regeneration Studies" *Dermatol Surg* 4021; 37:58-64. This document is incorporated herein by reference in its entirety.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIGS. 14A-14F are perspective views illustrating the working of the assembly of FIG. 3A;

FIG. 23A is a perspective view of the shaft of the assembly of FIG. 19 adapted with a single piercing member;

FIGS. 29A-29H are perspective views of parts of the assembly of FIG. 19 being engaged together;

DETAILED DESCRIPTION

Figure 1A:
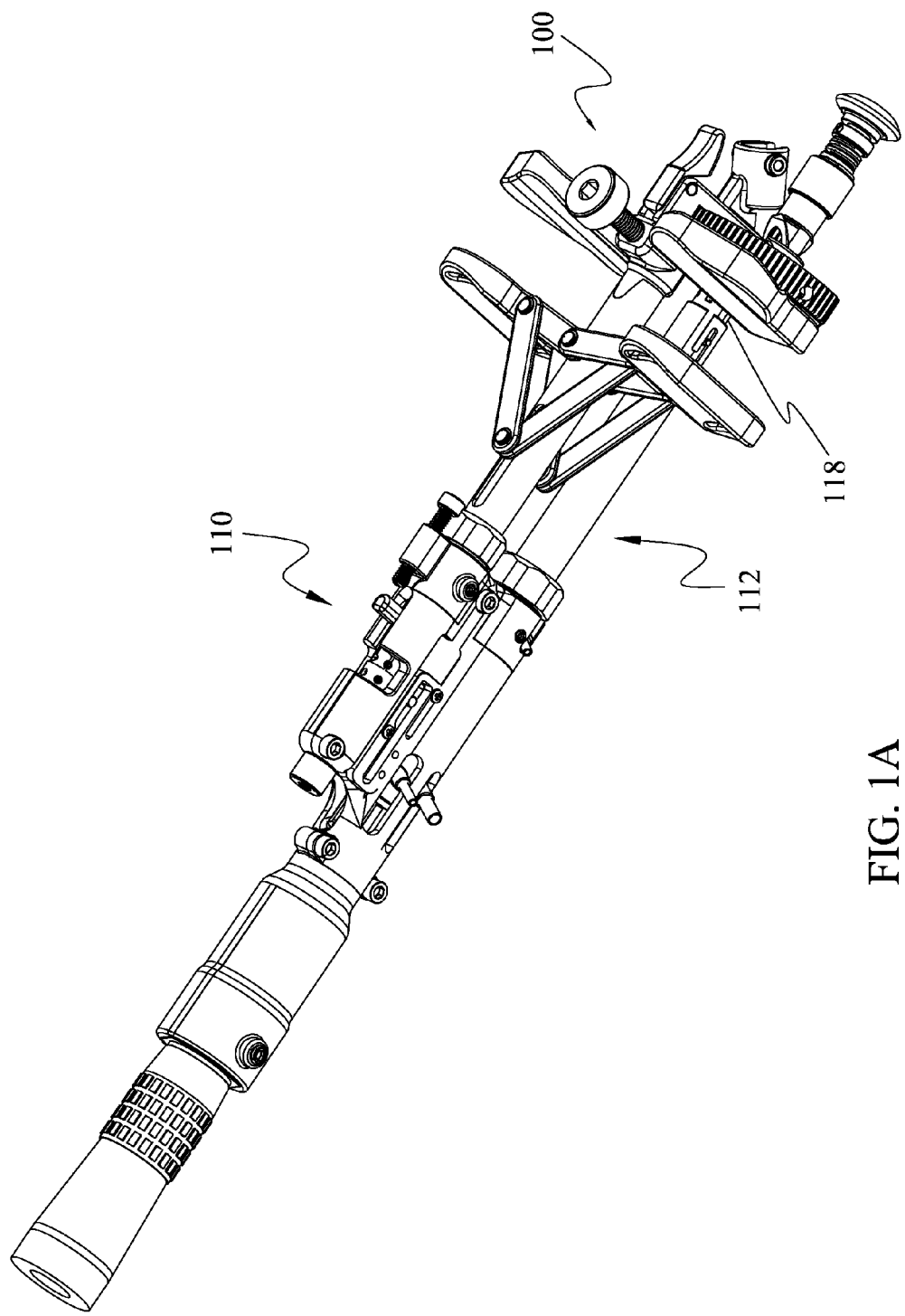
FIG. 1A is a perspective view of a device and a system.
Figure 1B:
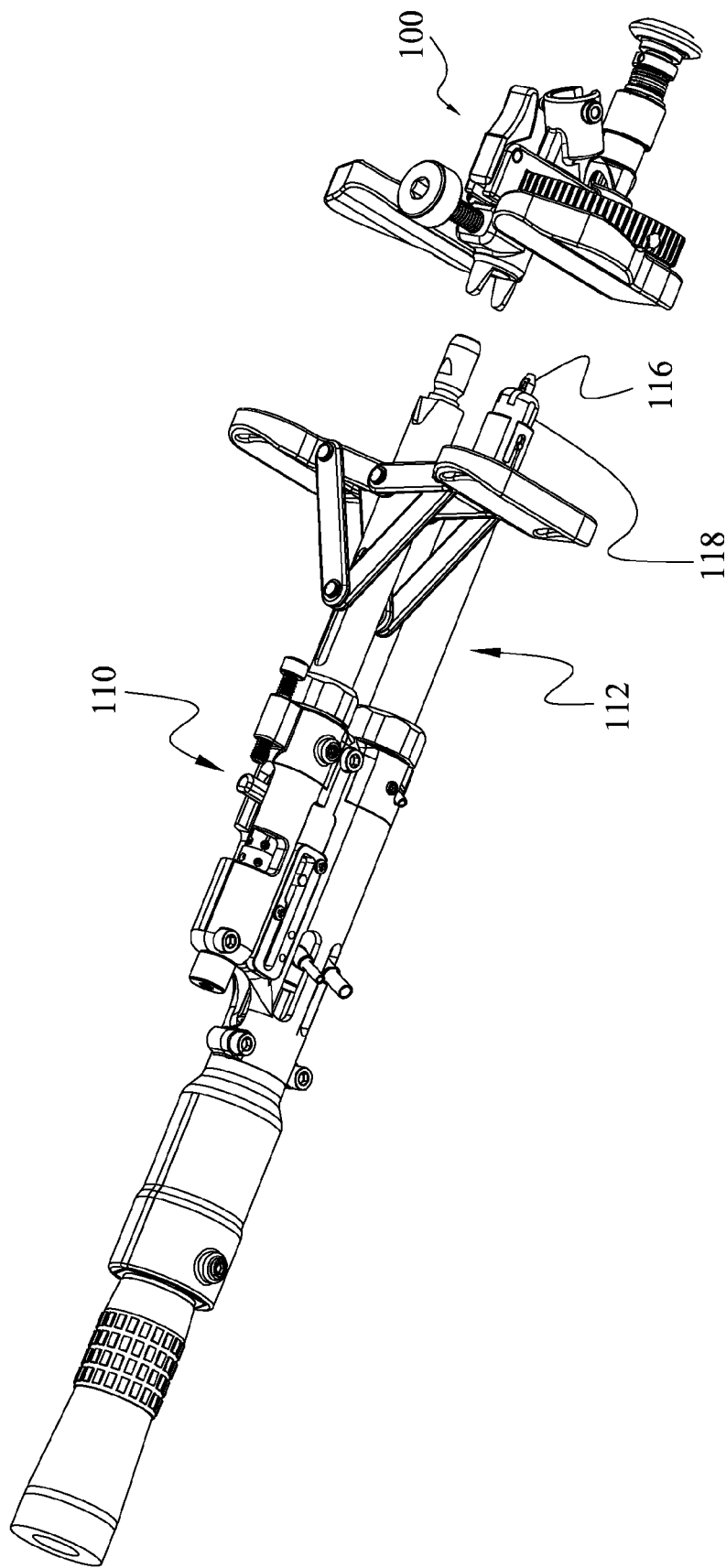
FIG. 1B is another perspective view of the device and system of FIG. 1A.
Figure 1C:
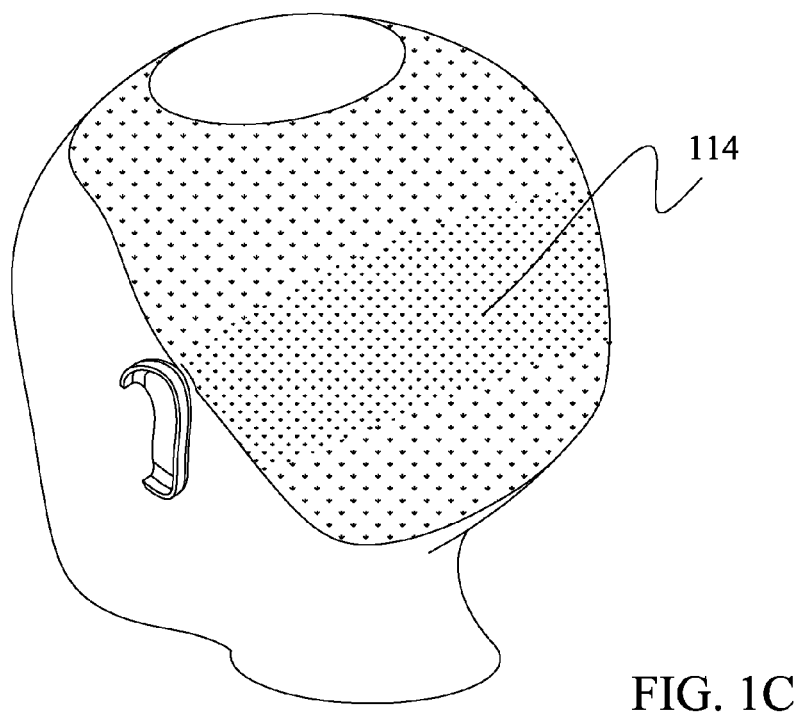
FIG. 1C is a perspective view of a human head.
Figure 1D:
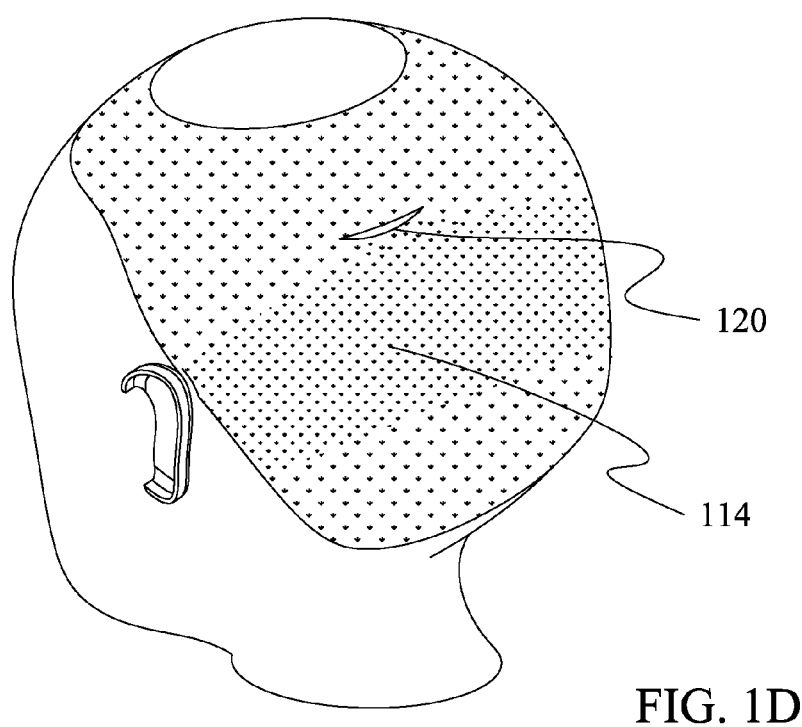
FIG. 1D is another perspective view of the human head of FIG. 1C in which an incision is made into the skin.
Figure 1E:
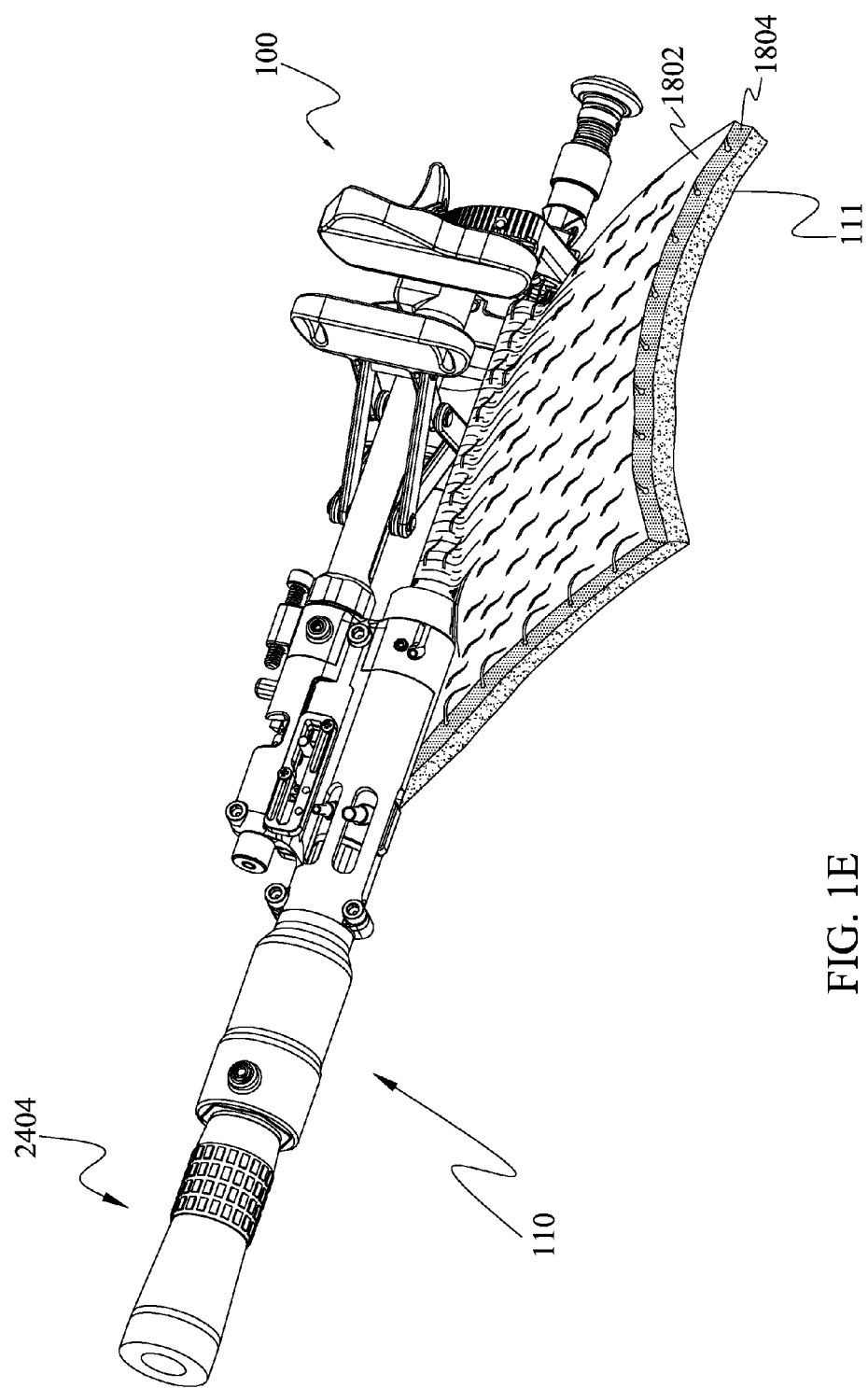
FIG. 1E is yet another perspective view of the device and system of FIG. 1A.

The disclosure may relate to altering the alignment of hair follicle with respect to a device that may be used for extraction of hair follicle. The device employed for extraction of hair follicle may be configured to extract hair follicle from underneath the external surface of the skin.

The following description illustrates principles, which may be applied in various ways to provide many different alternative embodiments. This description is not meant to limit the inventive concepts in the appended claims. The principles, structures, techniques, and methods disclosed herein may be adapted for use in other situations where a target tissue portion is to be extracted from a tissue region. For example, the present technology may be adapted for use in dermatology, cosmetic surgery, and/or general surgery. Although this disclosure focuses on extraction of head hair for subsequent transplantation, the disclosed technology also applies to extraction of hair follicles from other parts of the human body, such as the arm pit and pelvic regions, for the purpose of permanent hair removal. This technology also applies to extraction of other tissues, such as extraction of pathological tissues in the deeper layers of the skin or other body tissues, biopsy and/or removal of tissue being one example.

During extraction of a hair follicle, altering the alignment of the hair follicle to prevent follicle transection may be desired. Alteration of alignment may be achieved by employing a group of piercing members to manipulate a tissue such that it aligns with a device that may be employed for extraction of the hair follicle. While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. In addition, one of ordinary skill in the art will appreciate upon reading and understanding this disclosure that other variations for the technology described herein can be included within the scope of the present technology.

Referring to FIGS. 1A-1E, a system 100 for altering the alignment of hair follicles or tissue may be used. The system 100 may be used in conjunction with a device 110 that may be configured to extract a portion of the hair follicle or tissue from underneath the external surface 1802 of the skin 1804. The device 110 may be configured such that a portion 112 of the device 110 may be inserted under the skin 1804 to cut through a tissue at a donor region 114 of the head. The device 110 may include a first member 116 which may be used to extract a portion of the hair follicle. The device 110 may further include a tissue stabilizing member 118 which may be configured to apply pressure against or around a tissue comprising a hair follicle. The device 110 may be inserted into the area underneath the external surface 1802 of the skin 1804 by making an incision 120 on the external surface 1802 of the skin 1804 proximal or at the donor region 114. The first member 116 and the tissue stabilizing member 118 may enter the area underneath the external surface 1802 of the skin 1804. The first member 116 may include a cutting edge configured to cut through the tissue. The system 100 may be positioned external to the overlying surface of the skin opposite to the first member 116.

Figure 1F:
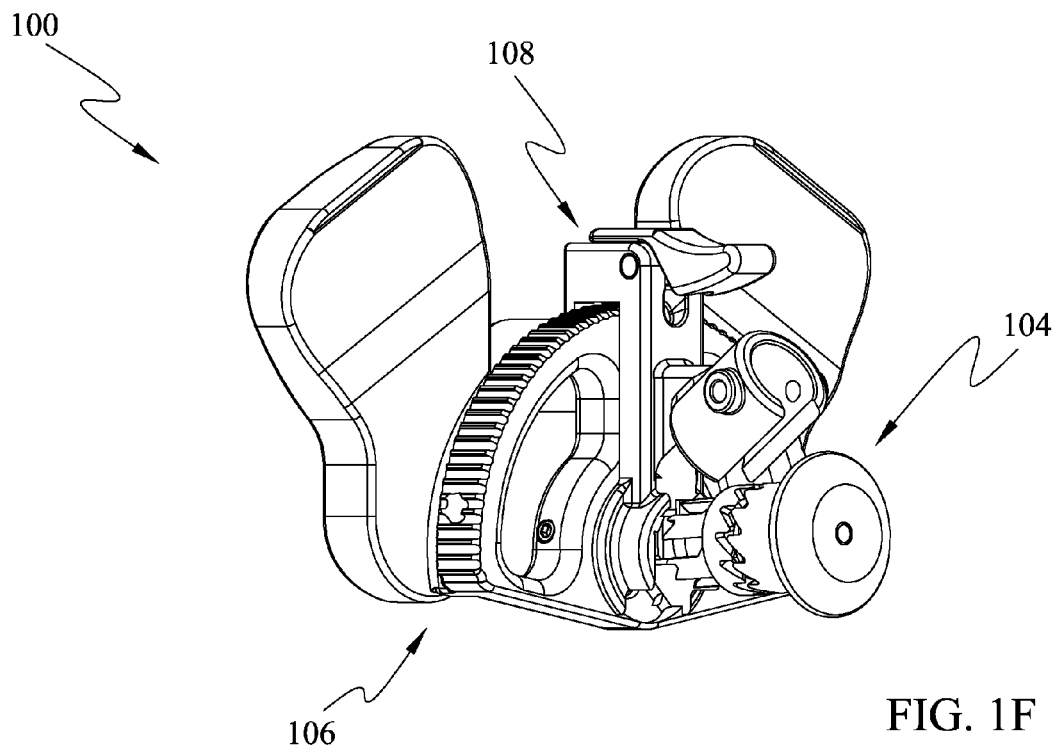
FIG. 1F is a perspective view of the system of FIG. 1A.
Figure 1G:
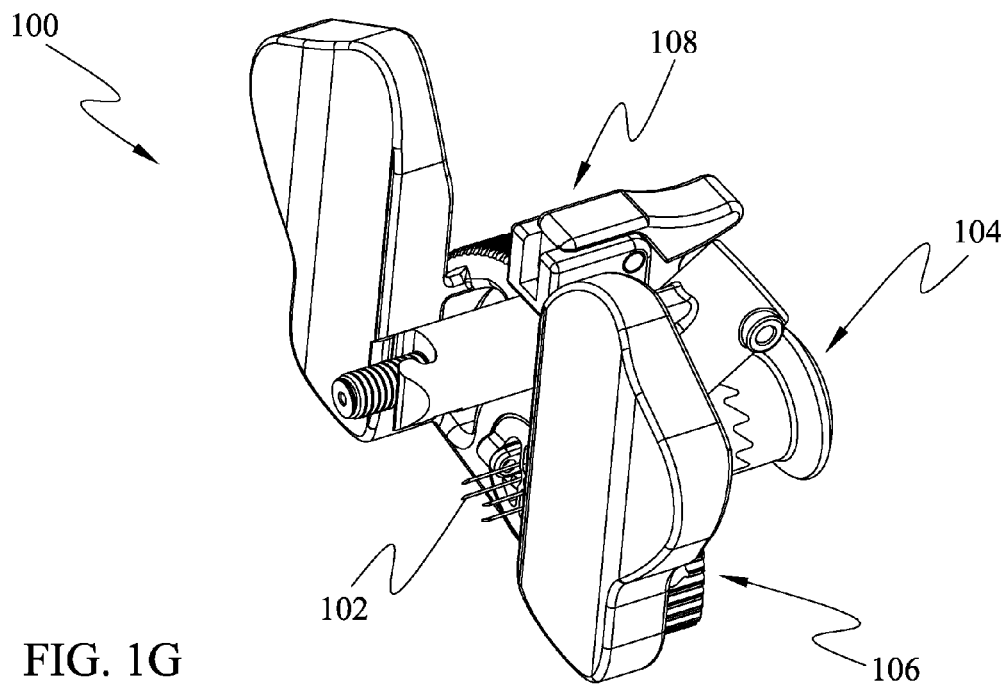
FIG. 1G is another perspective view of the system of FIG. 1A.

Referring to FIG. 1F-1G, the system 100 may include a plurality of piercing members 102, an assembly 104 for operating the piercing members 102, a guide member 106 and an arm 108. The piercing members 102 may be engaged to a shaft present in the assembly 104. The assembly 104 may be configured to operate the piercing members 102 to translate in a first direction towards the external surface of the skin. The translalory motion of the piercing members 102 in the first direction may allow the piercing members 102 to pierce into the skin 1804 through the external surface 1802 of the skin 1804. The piercing members 102 may assume an extended position after traversing in the first direction. The hair follicle to be extracted may be disposed between the plurality of the piercing members 102 such that the piercing members 102 may align the hair follicle by pivoting the piercing members 102. Once the hair follicle aligns with the first member 116, a portion of the hair follicle may be extracted from underneath the skin 1804 by the device 110. Upon completion of extraction, the piercing members 102 may be operated by the assembly 104 to translate in a second direction to assume a retracted position.

Figure 2:
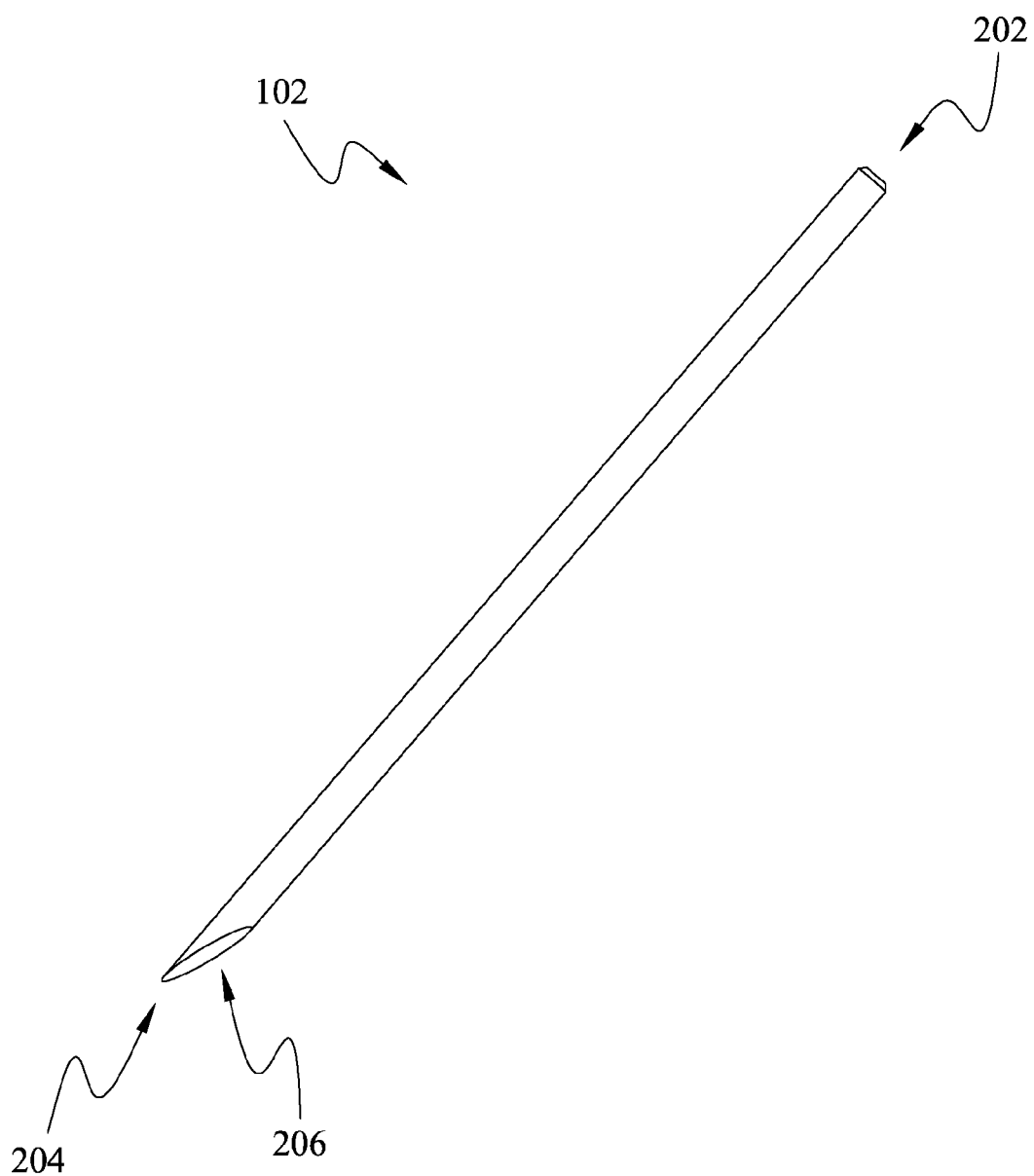
FIG. 2 is a perspective view of a piercing member of the system of FIG. 1A.

Referring to FIG. 2, the piercing member 102 or piercing means may include a proximal end 202 and a distal end 204. The piercing member 102 may be a needle defining a pointing distal end 204. The pointing distal end 204 may be achieved by providing a beveled configuration 206 towards the distal end 204. The pointed piercing member 102 may enable the piercing member 102 to be pierced through tissue. The piercing members 102 may be engaged to a part of the assembly 104 at the proximal end 202 of the piercing members 102.

Figure 3A:
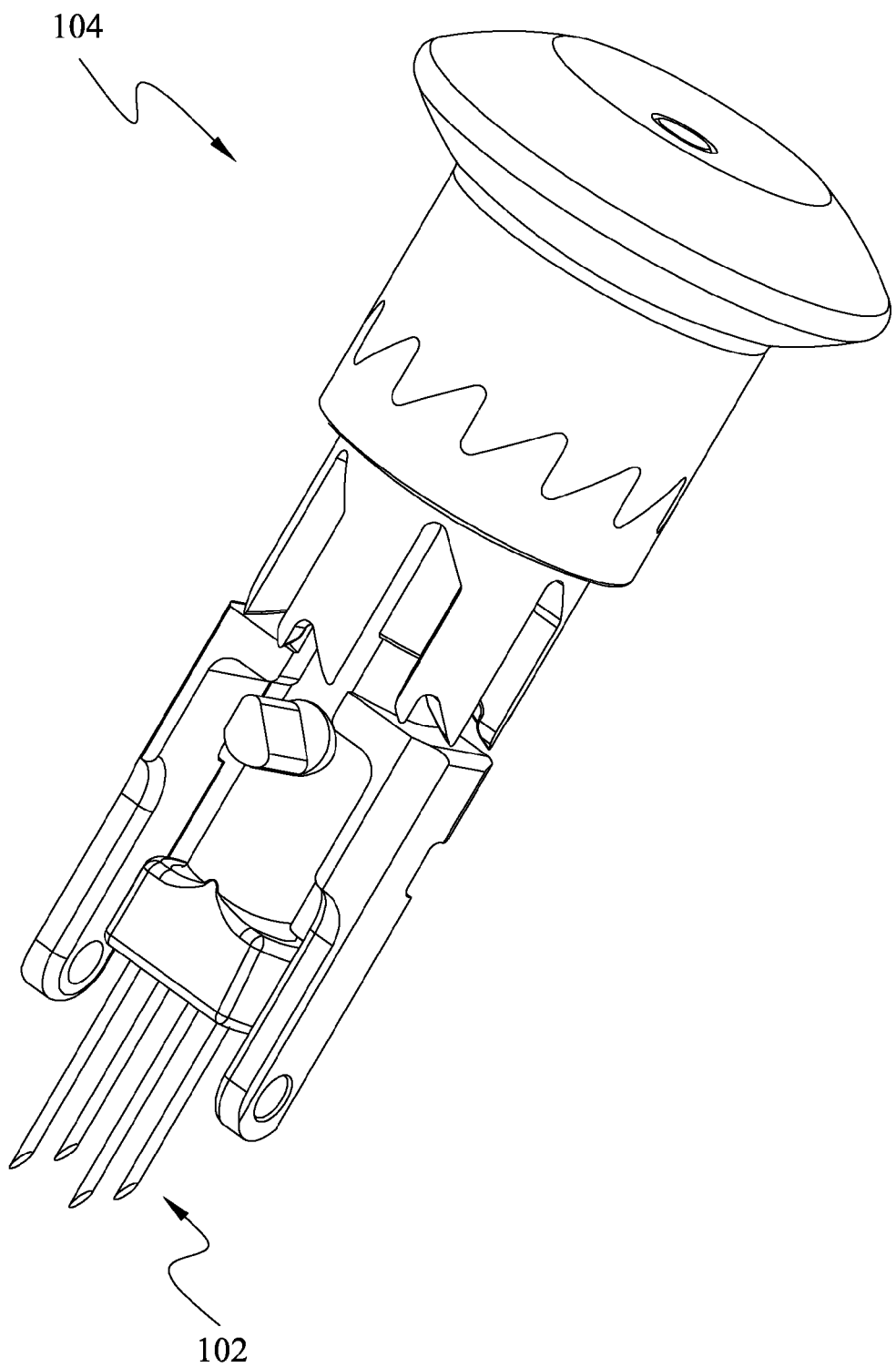
FIG. 3A is a perspective view of an assembly in the system of FIG. 1A.
Figure 3B:
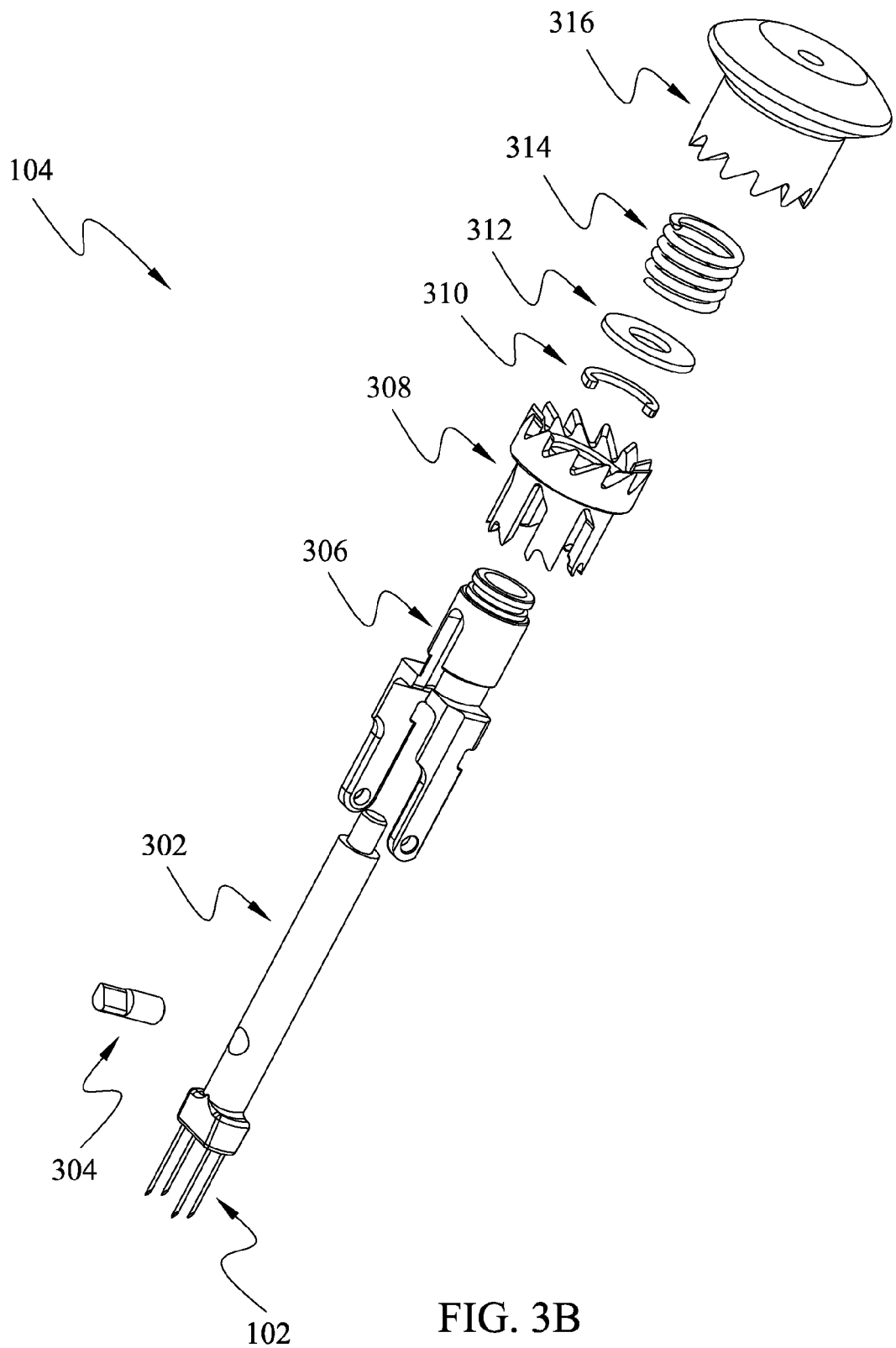
FIG. 3B is an exploded perspective view of the assembly of FIG. 3A.

Referring to FIG. 3A-3B, the assembly 104 or control means may be employed for receiving the piercing members 102 and operating the piercing members 102. The assembly 104 may include a shaft 302, an engagement member 304 or engagement means, a pivot enabling member 306 or pivot enabling means, a second engagement member 308, a first ring 310, a second ring 312 or washer, a compression member 314 and a cap 316.

The piercing members 102 may be made to pierce through the external surface 1802 of the skin 1804, by pressing the cap 316. Pressing of the cap 316 may push the shaft 302 towards the skin 1804, and may also enable partial rotation of the second engagement member 308, such that the engagement member 304 is aligned with one of a plurality of extended position lock slot 814 (illustrated in FIG. 8A) defined in the second engagement member 308. Releasing of the cap 316 may enable the shaft 302 to translate in a direction opposite to the direction in which it translated earlier. The translatory movement of the shaft 302 will be stopped by engagement of the engagement member 304 with the second engagement member 308 at the extended position lock slot 814, thereby enabling the piercing members 102 to assume an extended position.

The piercing members 102 may be made to retract out of the tissue from the extended position to a retracted position, by pressing the cap 316. Pressing of the cap 316 pushes the shaft 302 further, thereby disengaging the engagement member 304 from the second engagement member 308. Pressing of the cap 316 may also enable partial rotation of the second engagement member 308, such that the engagement member 304 is now aligned with one of the retracted position lock slot 816 (illustrated in FIG. 8A) defined in the second engagement member 308. Releasing of the cap 316 will enable the piercing members 102, along with the shaft 302 to translate out of the tissue. The translatory movement of the shaft 302 may be stopped by engagement of the engagement member 304 with the second engagement member 308 at one of the plurality of retracted position lock slot 816, thereby enabling the piercing members 102 to assume the retracted position.

Figure 4:
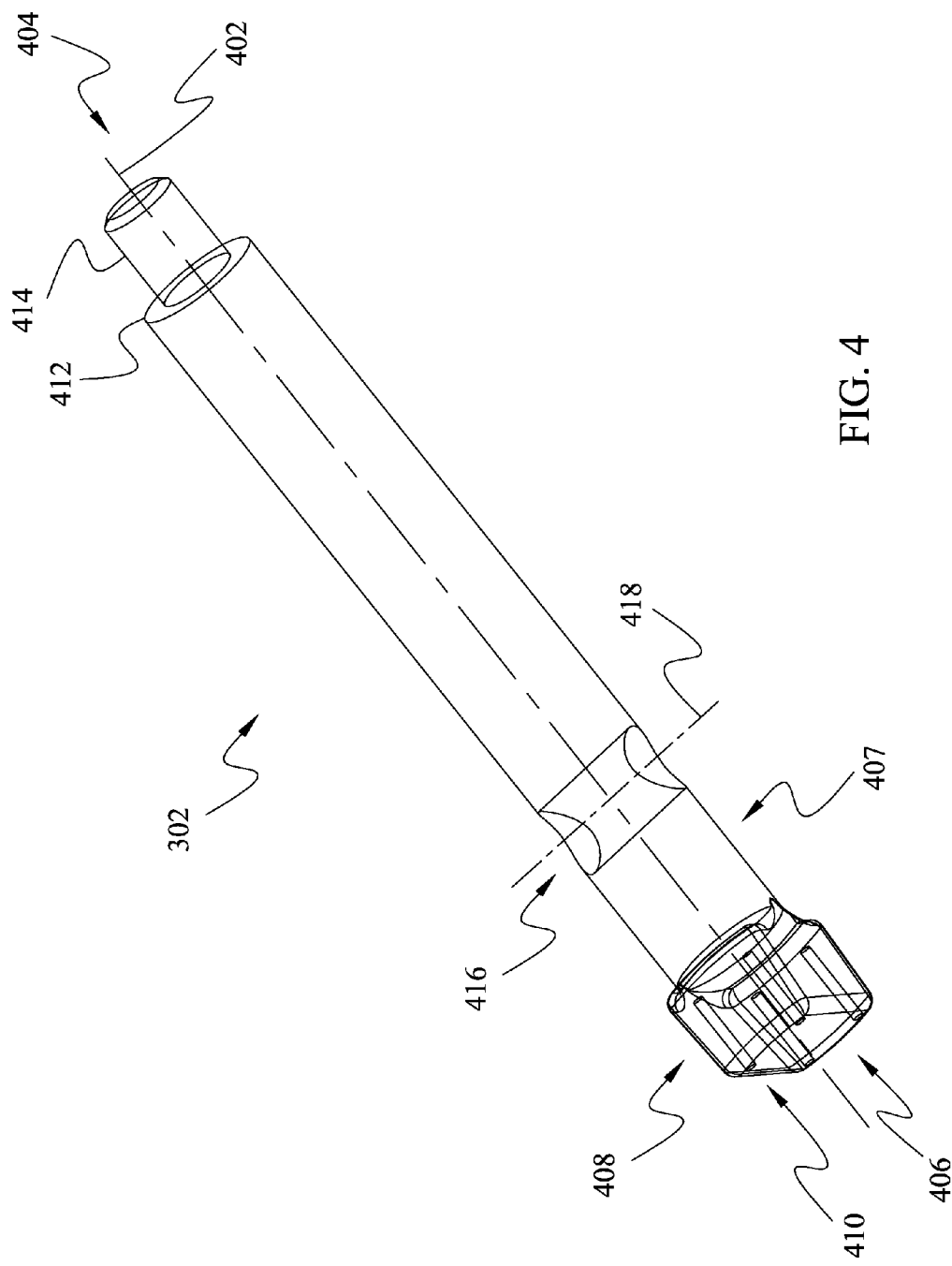
FIG. 4 is a perspective view of a shaft of the assembly of FIG. 3A.

Referring to FIG. 4, a substantial portion of the shaft 302 may define a cylindrical cross section along its longitudinal axis 402. The shaft 302 may be constructed to have any other suitable cross section, such as a polygonal cross section. The shaft 302 may include a proximal end 404 and a distal end 406. The shaft 302 may include a base 408 at the distal end 406. The base 408 may be such that, cross sectional area of the base 408 may be greater than the cross sectional area of a portion 407 of the shaft 302 that is present immediately after the base 408. In an embodiment, the base 408 may be such that, cross sectional area of the base 408 may be greater than the cross sectional area of rest of the shaft 302 about the longitudinal axis 402. The above mentioned exemplary configuration may enable the assembly 104 to have a relatively smaller footprint, while enabling the piercing members to be spread about a larger cross sectional area. The base 408 of the shaft 302 may comprise a plurality of first apertures 410 extending from the distal end 406 into the shaft 302 parallel to the longitudinal axis 402. The apertures 410 may be configured to accommodate the piercing members 102 such that a portion of the piercing members 102 may be accommodated in the first apertures 410, and a remaining portion which includes the pointed distal end 204 may protrude out of the shaft 302.

In an embodiment, the base 408 and the piercing members 102 may be configured such that, one or more piercing members 102 diverge as they extend away from the base 408.

In another embodiment, the base 408 and the piercing members 102 may be configured such that, one or more piercing members 102 converge as they intersect with the base 408.

The shaft 302 may define a shoulder 412 towards the proximal end 404. Further, the shaft may include a neck 414, which may extend from the shoulder 412 towards the proximal end 404 of the shaft 302. The neck 414 may be cylindrical in shape, or may have any other suitable shape. The neck 414 may have a diameter smaller than the diameter of the portion of the shaft 302 immediately preceding it.

The shaft 302 may define a second aperture 416, comprising a longitudinal axis 418. The axis 418 of the second aperture 416 and the longitudinal axis 402 of the shaft 302 may intersect with each other. The axis 418 of the second aperture 416 and the longitudinal axis 402 of the shaft 302 may be orthogonal to each other. The second aperture 416 may be configured to accommodate the engagement member 304.

Figure 5A:
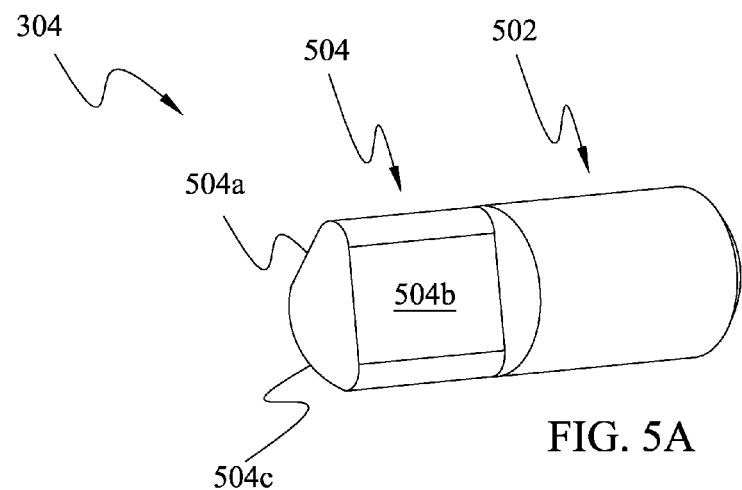
FIGS. 5A-5C are perspective views of an engagement member of the assembly of FIG. 3A.
Figure 5B:
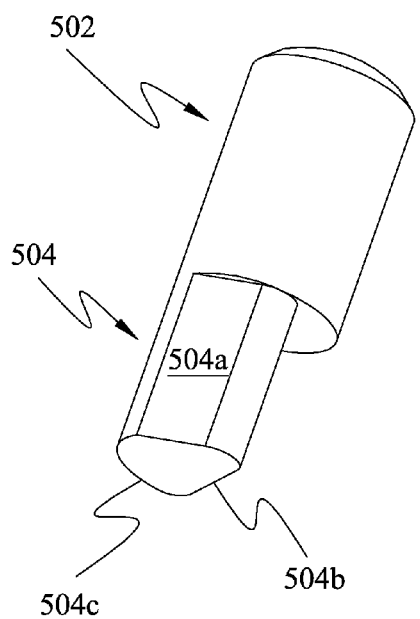
Figure 5C:
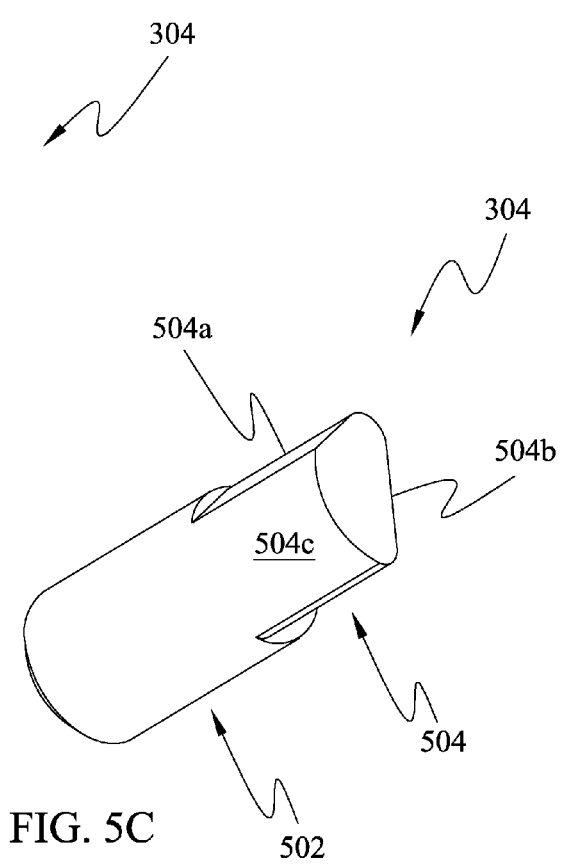

Referring to FIGS. 5A-5C, the engagement member 304 may include an insertion portion 502 and a protrusion portion 504. The insertion portion 502 of the engagement member 304 may be configured to be accommodated within the second aperture 416 defined in the shaft 302. The insertion portion 502 of the engagement member 304 may have a cylindrical cross section. Alternatively, the cross section of the insertion portion 502 may be polygonal, and the second aperture 416 may define a complimentary cross section. The insertion portion 502 may be accommodated within the second aperture 416 by means of a friction fit, press fit or interference fit, among other means of engagement.

The protrusion portion 504 of the engagement member 304 may be configured such that when the insertion portion 502 is accommodated within the second aperture 416, the protrusion portion 504 protrudes out of the shaft 302. The shape of the protrusion portion 504 may be such that it engages with any one of the extended position lock slot 814 and the retracted position lock slot 816 to enable the piercing members 102 to assume the extend position or retracted position.

The protrusion portion 504 may extend from the insertion portion 502. The protrusion portion 504 may have "V" or "U" shaped cross section. The "V" or "U" shaped configuration may be asymmetrical. The protrusion portion 504 may include a first surface 504a, a second surface 504b and a third surface 504c. The first surface 504a and the second surface 504b may intersect to define the "V" shaped cross section. Further, the third surface 504c may intersect the first surface 504a and the second surface 504b. One of the more intersections between the first surface 504a, the second surface 504b and the third surface 504c may define curved, transitory or smooth edges or angles. Alternatively, one or more intersections between the first surface 504a, the second surface 504b and the third surface 504c may define hard angles or sharp edges.

Figure 6:
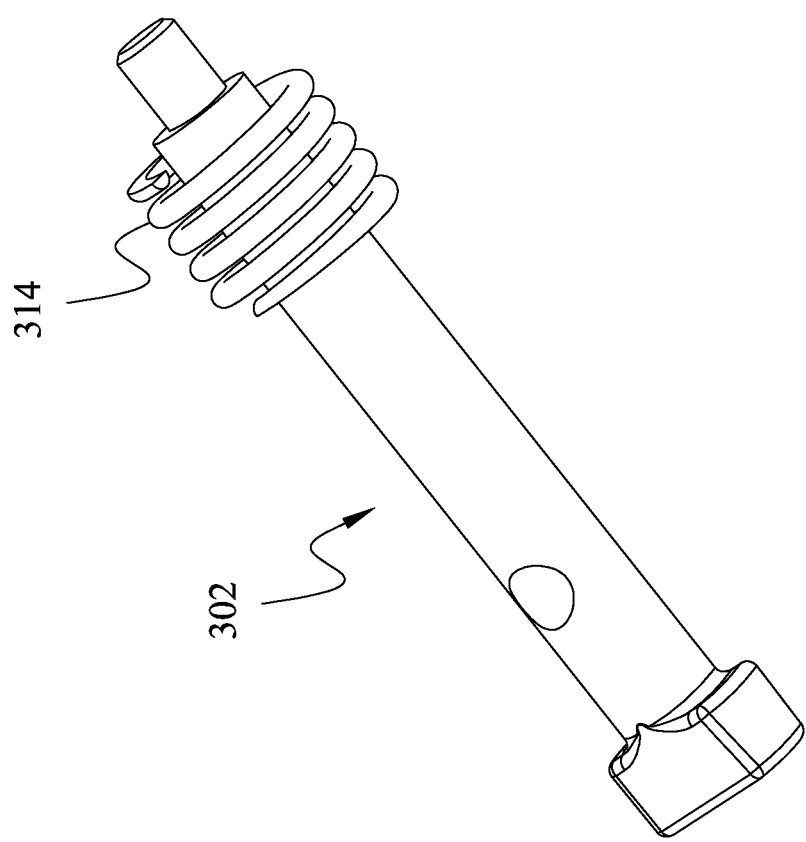
FIG. 6 is a perspective view of the shaft and a compression member of the assembly of FIG. 3A.

Referring to FIG. 6, the compression member 314 may be a helical spring 314. The compression member 314 may be dimensioned such that it may encircle a portion of the shaft 302 between the proximal end 404 and the distal end 406 of the shaft 302. The shaft 302 may translate along a longitudinal axis of the compression member 314. The longitudinal axis of the compression member 314 and the longitudinal axis of the shaft 302 may coincide. The compression member 314 may enable the shaft 302 to retract along the longitudinal axis 402 of the shaft 302.

Figure 7A:
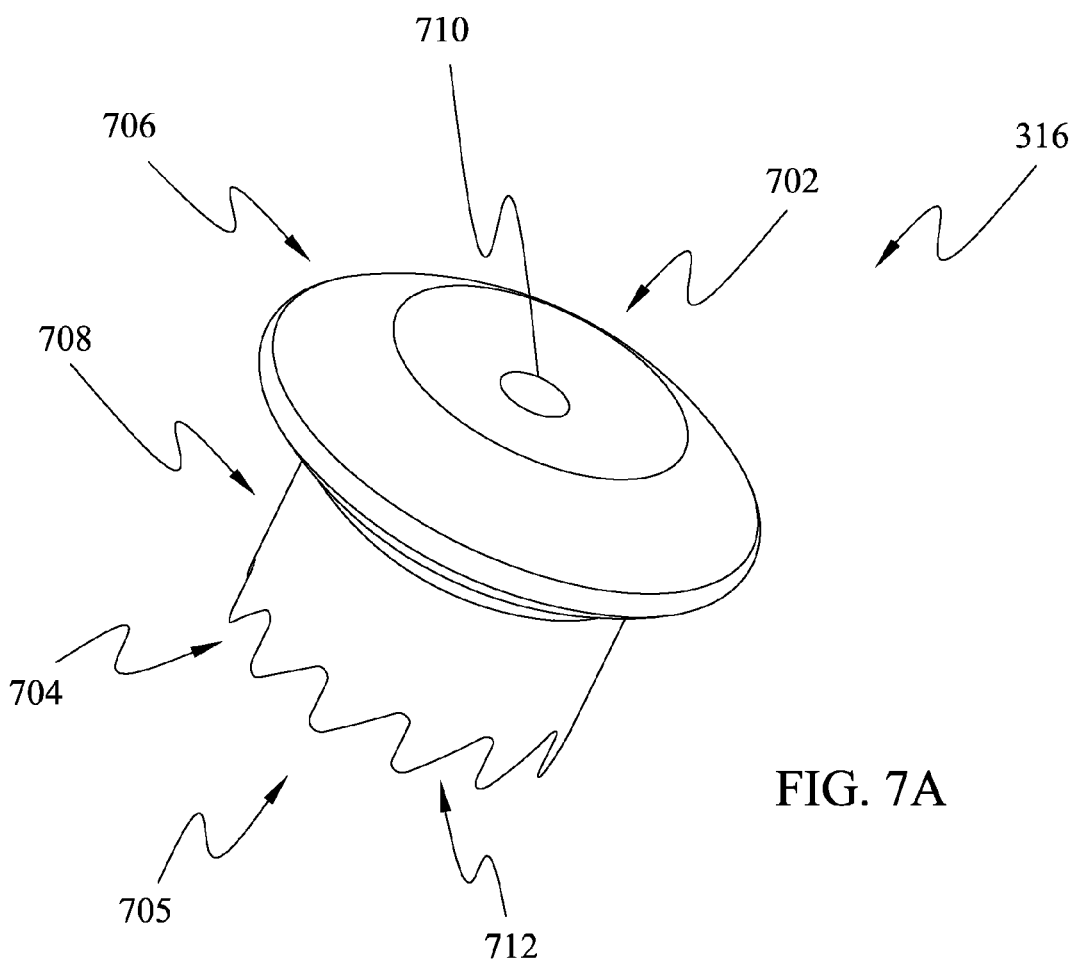
FIG. 7A is a perspective view of a cap of the assembly of FIG. 3A.
Figure 7B:
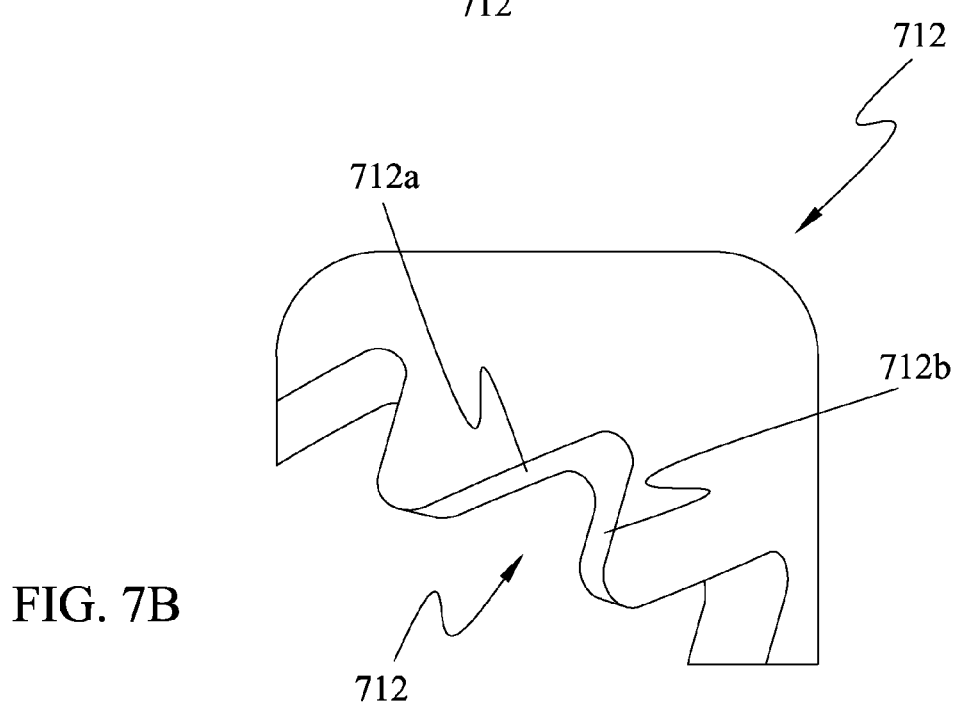
FIG. 7B is a perspective view of teeth provided of the cap of FIG. 7A.

The shaft 302 may be rigidly engaged with the cap 316. The cap 316 may be configured to receive the neck 414 of the shaft 302. Referring to FIGS. 7A-7B, the cap 316 may include a proximal end 702 and a distal end 704. The cap 316 may include a lid portion 706 and a cover portion 708. The lid portion 706 may be provided towards the proximal end 702 of the cap 316. The cover portion 708 may extend from the lid portion 706 towards the distal end 704, such that an empty space 705 is defined by the lid portion 706 and the cover portion 708. The lid portion 706 may define an aperture 710. The aperture 710 may extend from an inside surface of the lid portion 706 towards an outside surface of the lid portion 706. The aperture 710 may be configured to accommodate the neck 414 of the shaft 302. The neck 414 may be engaged, for example by press or interference fitting with the cap 316, among other means of engagement.

The cover portion 708 may define teeth 712 extending towards the distal end 704 of the cap 316. Each tooth 712 may be formed by a first surface 712a intersecting with a second surface 712b to define an asymmetrical "V" shaped tooth. The first surface 712a may be beveled. The teeth 712 defined in the cap 316 may interface with corresponding teeth defined in the second engagement member 308.

Figure 8A:
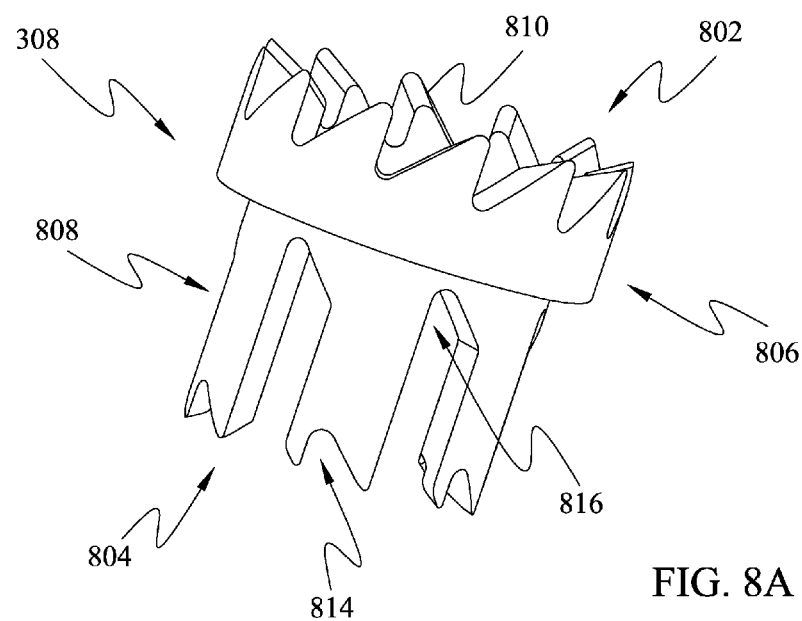
FIG. 8A is a perspective view of a second engagement member of the assembly of FIG. 3A.
Figure 8B:
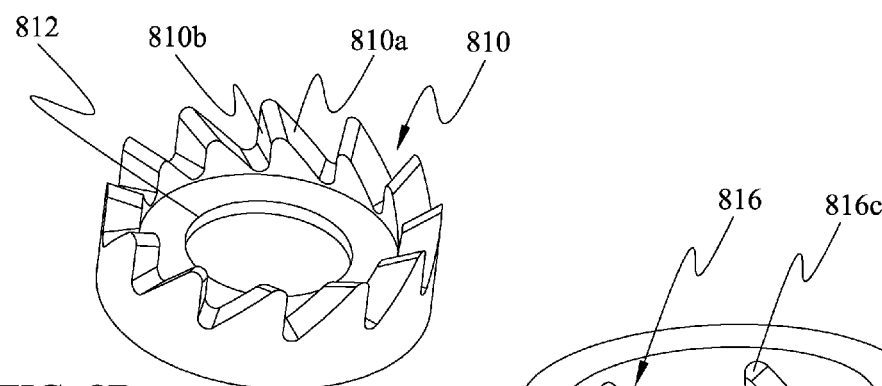
FIG. 8B is a perspective view of teeth provided in the second engagement member of FIG. 8A.
Figure 8C:
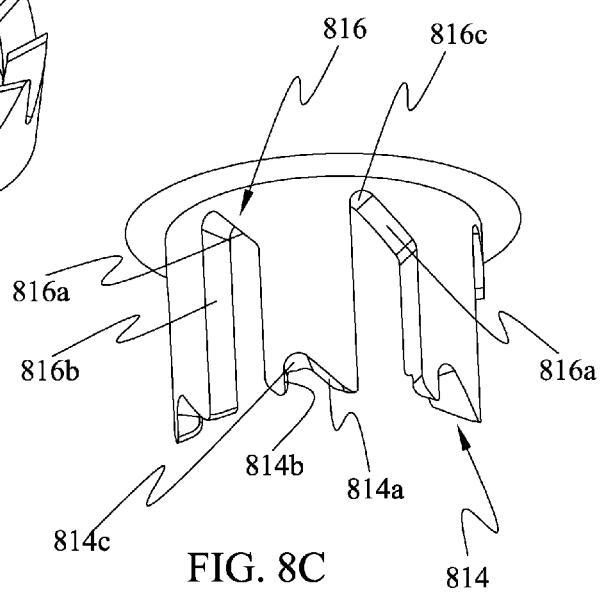
FIG. 8C is a perspective view of second engagement member arms provided in the second engagement member of FIG. 8A.

Referring to FIGS. 8A-8C, the second engagement member 308 may include a proximal end 802 and a distal end 804. The second engagement member 308 may include a head 806 and a plurality of second engagement member arms 808. The head 806 may be provided towards the proximal end 802 of the second engagement member 308. The second engagement member arms 808 may extend from the head 806 towards the distal end 804 of the second engagement member 308. The head 806 may define teeth 810 complimentary to the teeth 712 defined in the cap 316. Each tooth 810 may be formed by a first surface 810a intersecting with a second surface 810b to define an asymmetrical "V" shaped tooth. The first surface 810a may be beveled. The teeth 810 defined in the second engagement member 308 may interface with corresponding teeth 712 defined in the cap 316.

The head 806 may define a ring 812 surrounded by the teeth 810. The teeth 810 may extend in a first direction towards the proximal end 802 from the ring 812, while the second engagement member arms 808 may extend in a second direction towards the distal end 804 from the ring 812. Each second engagement member arms 808 may define an extended position lock slot 814, while adjacent second engagement member arms 808 may define a retracted position lock slot 816. Each of the extended position lock slots 814 and the retracted position lock slot 816 may be complimentary to the shape of the protrusion portion 504, such that each of the slots 814, 816 is configured to receive the protrusion portion 504 of the engagement member 304.

Each of the slots 814 may have "V" or "U" shaped cross section. The "V" or "U" shaped configuration may be asymmetrical. Each slot 814 may be defined by a first surface 814a and a second surface 814b. The first surface 814a may be beveled. The first surface 814a and the second surface 814b may intersect to define the "V" shaped cross section. The intersection between the first surface 814a and the second surface 814b may define curved, transitory or smooth edges or angles. Alternatively, the intersection between the first surface 814a and the second surface 814b may define hard angles or sharp edges. Similarly, slots 816 may be defined by first surface 816a and a second surface 816b. The intersection 816c of the "V" configuration in slot 816 is closer to the proximal end 802 or ring 812 when compared with intersection 814c of the "V" configuration in slot 814. The intersection 814c of the "V" configuration in slot 814 is closer to the distal end 804 when compared with intersection 816c of the "V" configuration in slot 816.

Figure 9:
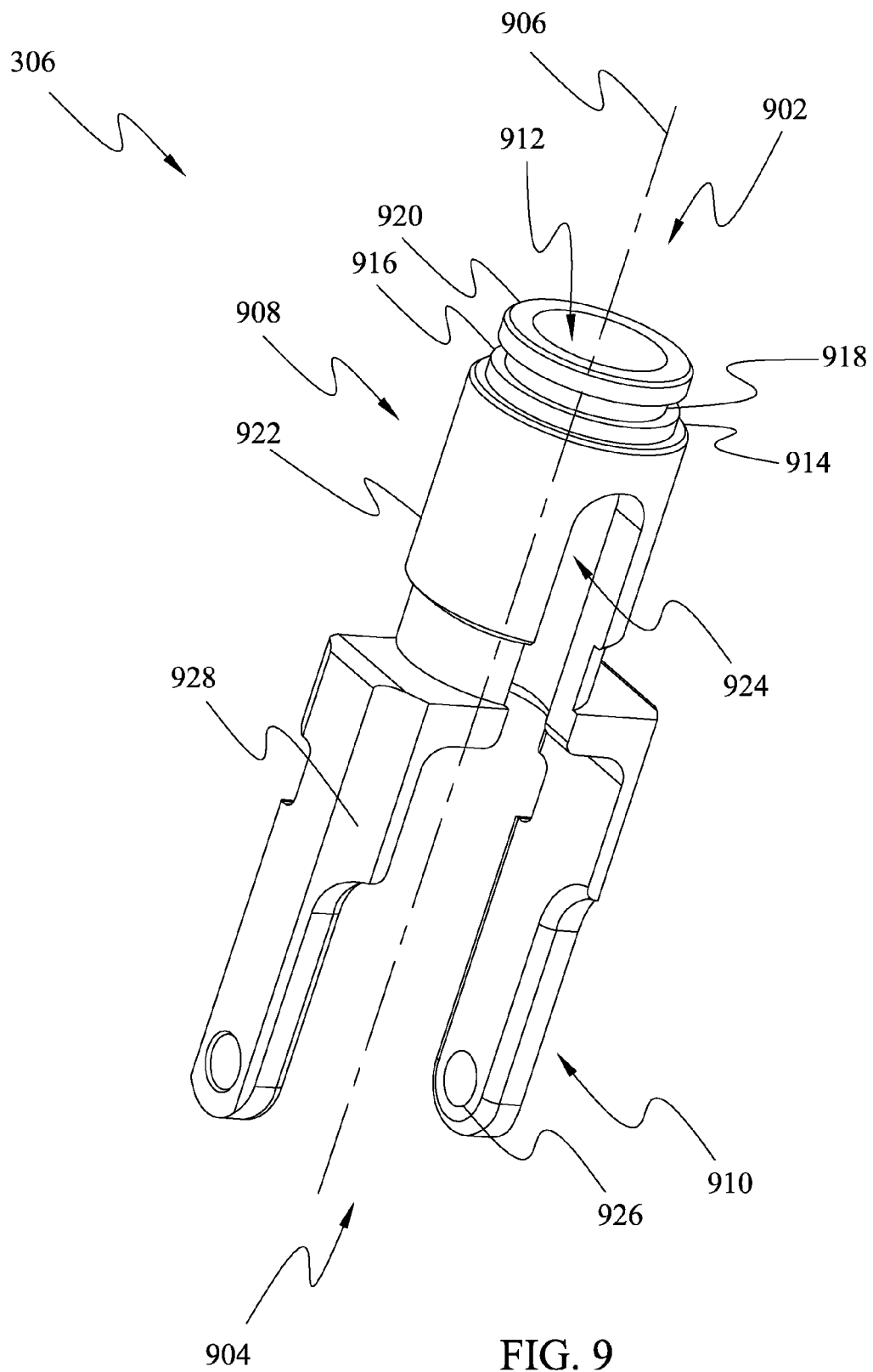
FIG. 9 is a perspective view of a pivot enabling member of the assembly of FIG. 3A.

Referring to FIG. 9, the pivot enabling member 306 may have a proximal end 902, a distal end 904 and a longitudinal axis 906. The pivot enabling member 306 may include a pivot enabling member head 908 and a pair of pivot enabling member arms 910. The pivot enabling member head 908 may define a through hole 912 configured to allow the shaft 302 to translate along the axis 906. The pivot enabling member head 908 may include a shoulder 914, a first neck 916, a second neck 918 and a head 920. The first neck 916 may extend from the shoulder 914, the second neck 918 may extend from the first neck 916, and the head 920 may extend from the second neck 918. The first neck 916 may have a diameter that is smaller than the diameter of the shoulder 914. The second neck 918 may have a diameter that is smaller than the diameter of the first neck 916. The head 920 may have a diameter that is larger than the diameter of the second neck 918. The first ring 310, which may be a retention ring, may be engaged around the second neck 918. The second ring 312 may be disposed on top of the head 920.

The pivot enabling member head 908 may have a cylindrical body 922 extending along the axis 906. The cylindrical body 922 may define a slot 924 extending along the axis 906, such that the slot 924 has an open end towards the distal end 904.

The arms 910 may extend from the pivot enabling member head 908 towards the distal end 904. Each of the arms 910 may define apertures 926 configured to engage with pivot pins, thereby enabling the pivot enabling member 306 to pivot.

Figure 11A:
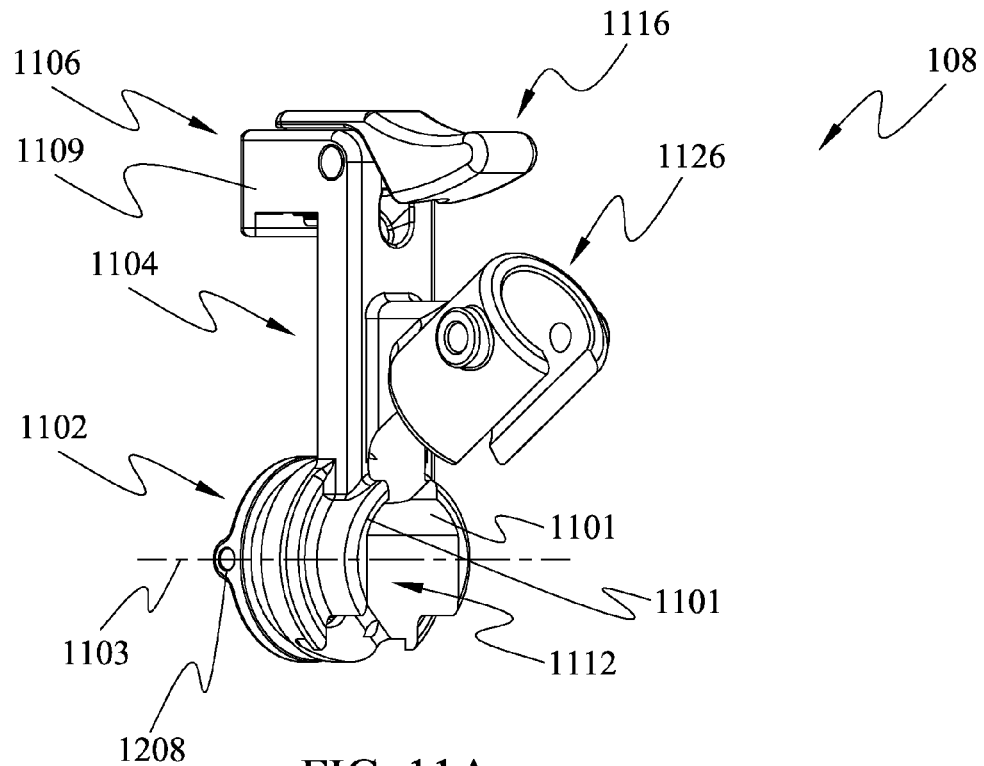
FIG. 11A is a perspective view of an arm of the system of FIG. 1F.
Figure 11B:
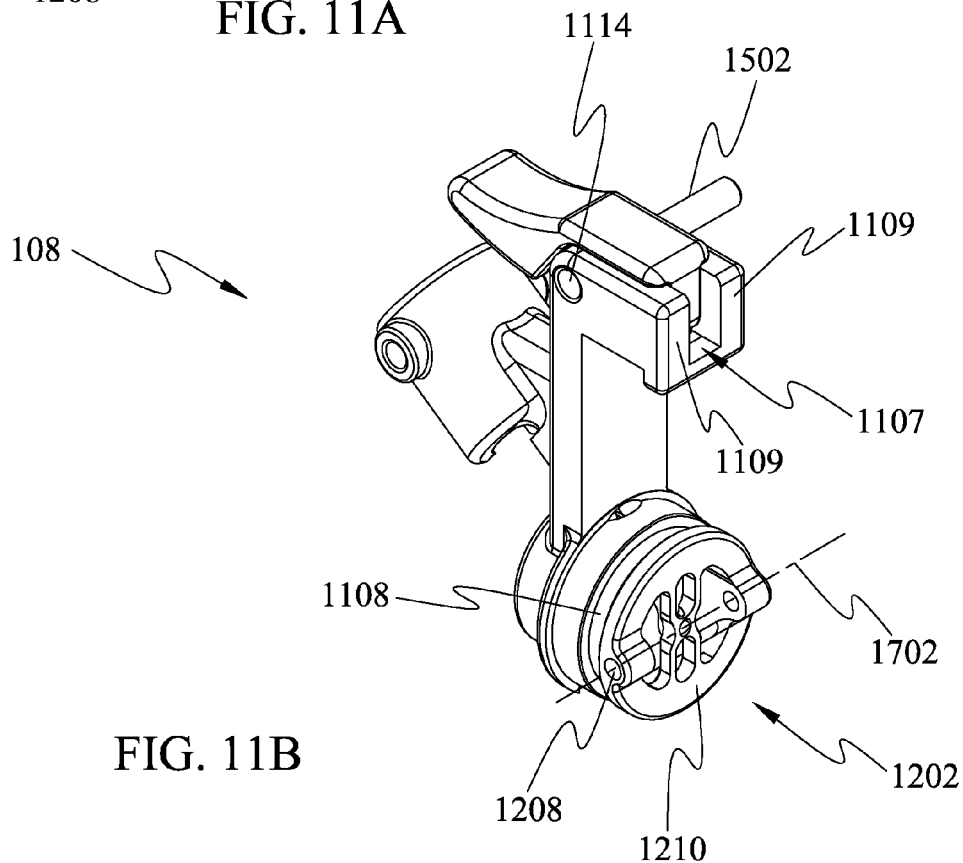
FIG. 11B is another perspective view of the arm of the system of FIG. 1F.
Figure 12A:
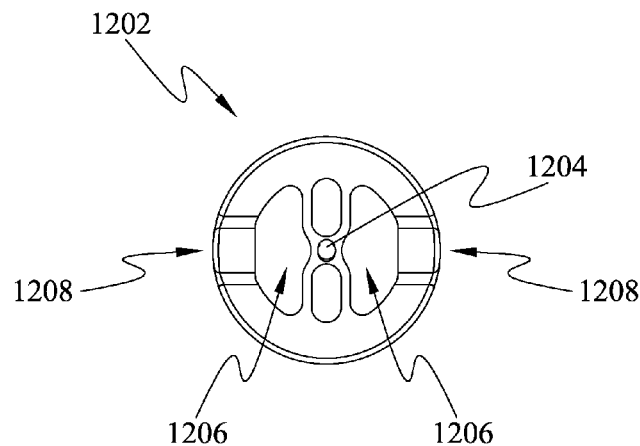
FIG. 12A is a back view of a counter pressure device of the system of FIG. 1F.
Figure 12B:
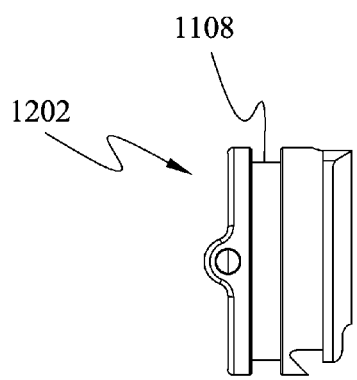
FIG. 12B is a side view of the counter pressure device of the system of FIG. 1F.
Figure 12C:
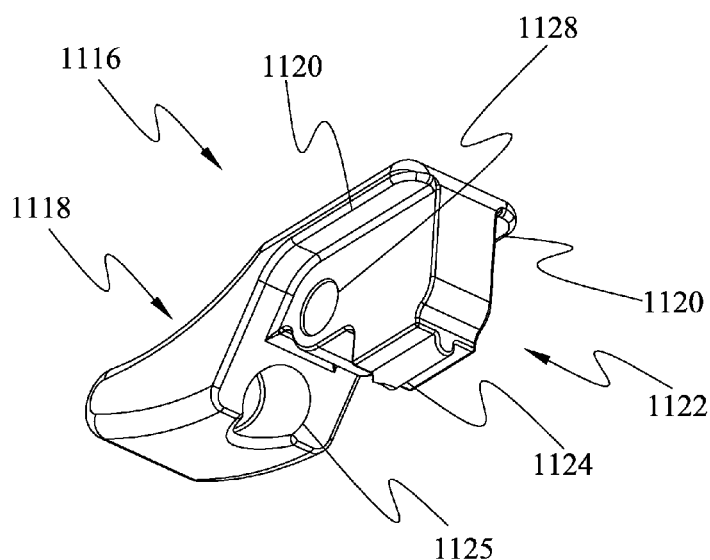
FIG. 12C is a perspective view of latch of the arm of FIG. 11A.
Figure 12D:
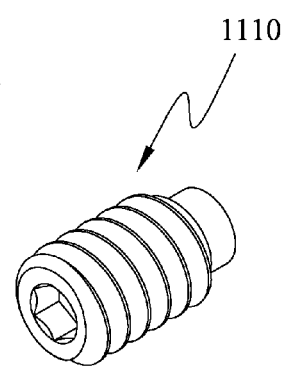
FIG. 12D is a perspective view of an engagement screw of the system of 1F.
Figure 13A:
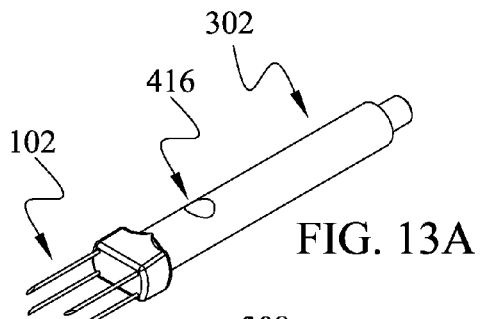
FIGS. 13A-13H are perspective views of parts of the assembly of FIG. 3A being engaged together.
Figure 13B:
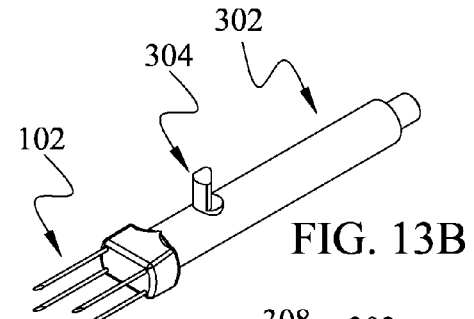
Figure 13C:
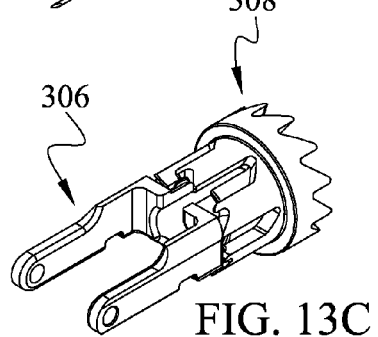
Figure 13D:
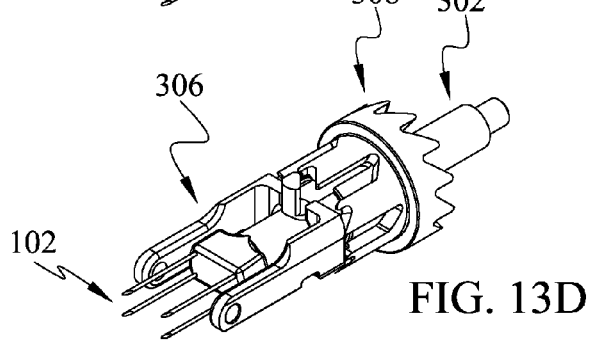
Figure 13E:
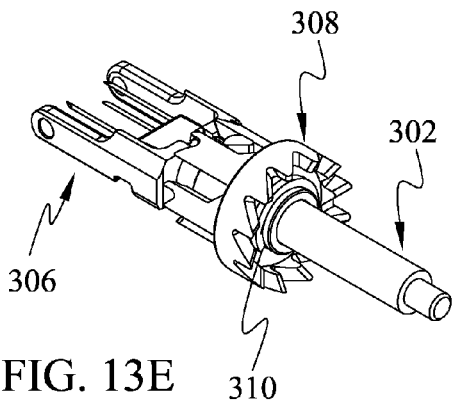
Figure 13F:
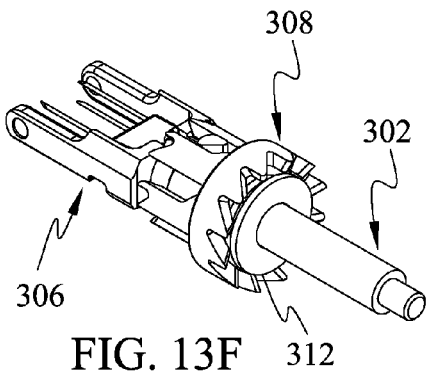
Figure 13G:
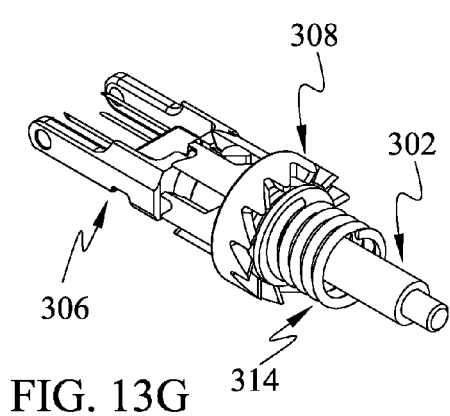
Figure 13H:
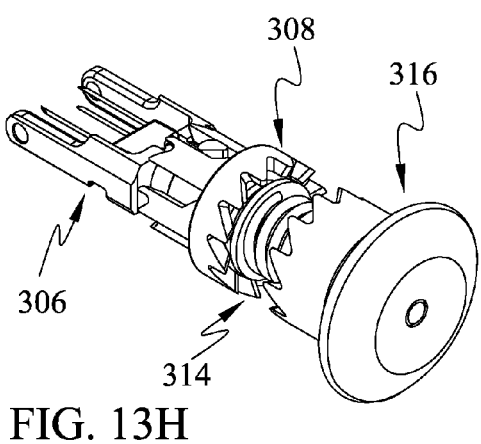
Figure 15A:
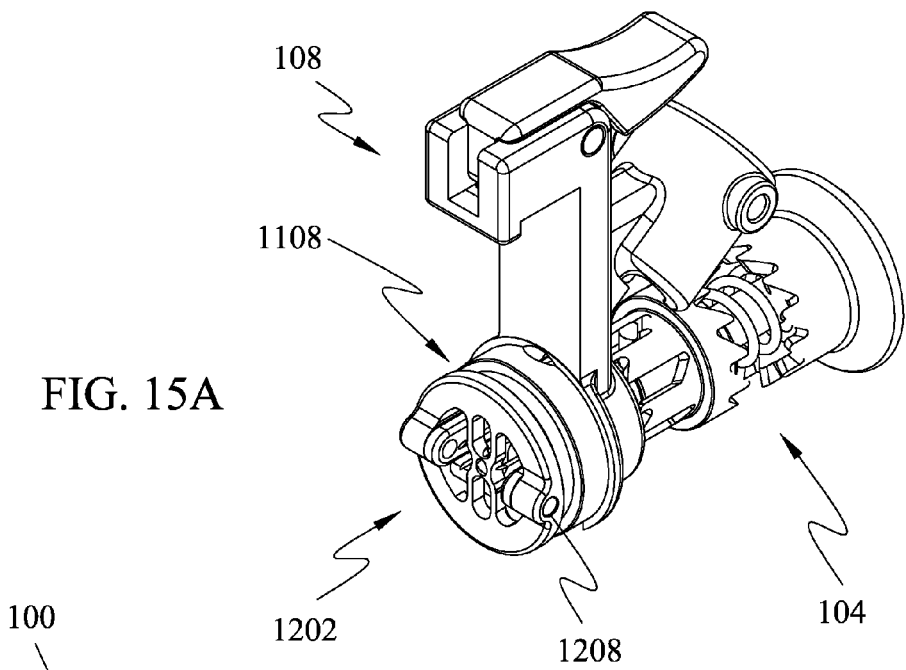
FIG. 15A is a perspective view of the arm and the assembly of the system of FIG. 1F.
Figure 15B:
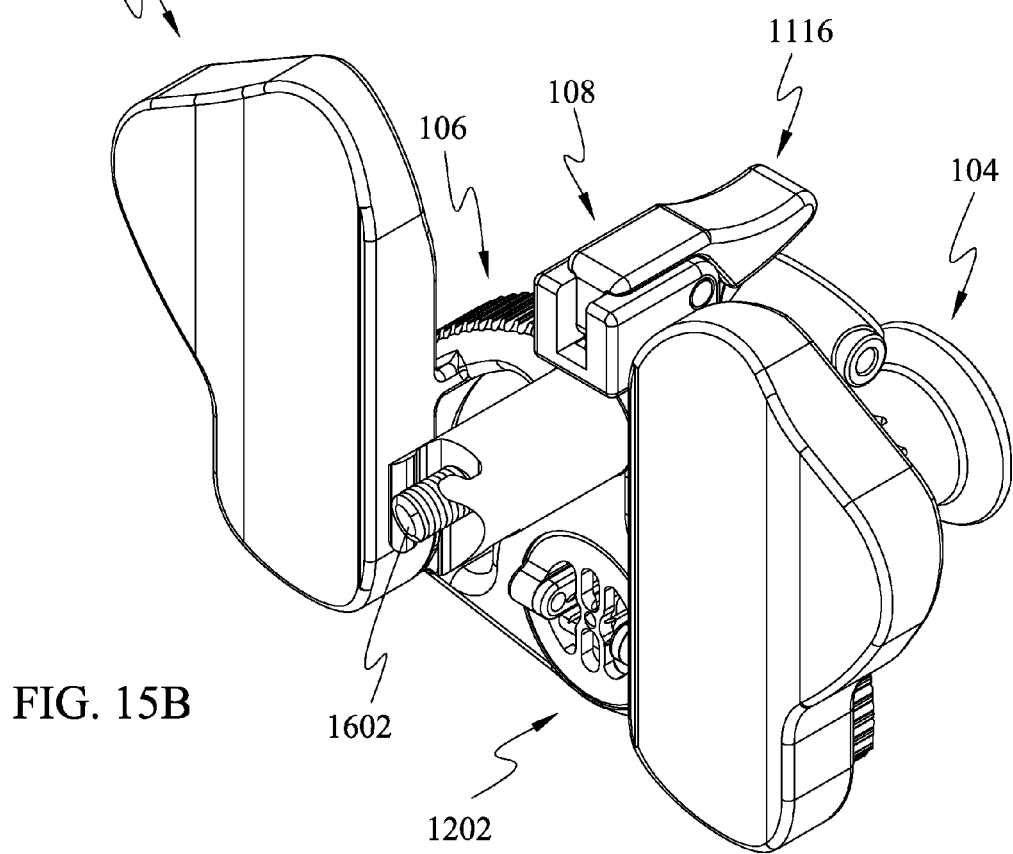
FIG. 15B is another perspective view of the system of FIG. 1F.
Figure 16A:
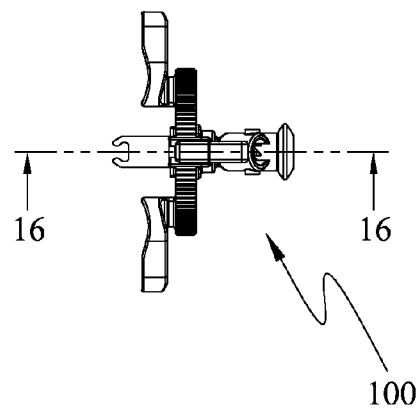
FIG. 16A is a top view of the system of FIG. 1F.
Figure 16B:
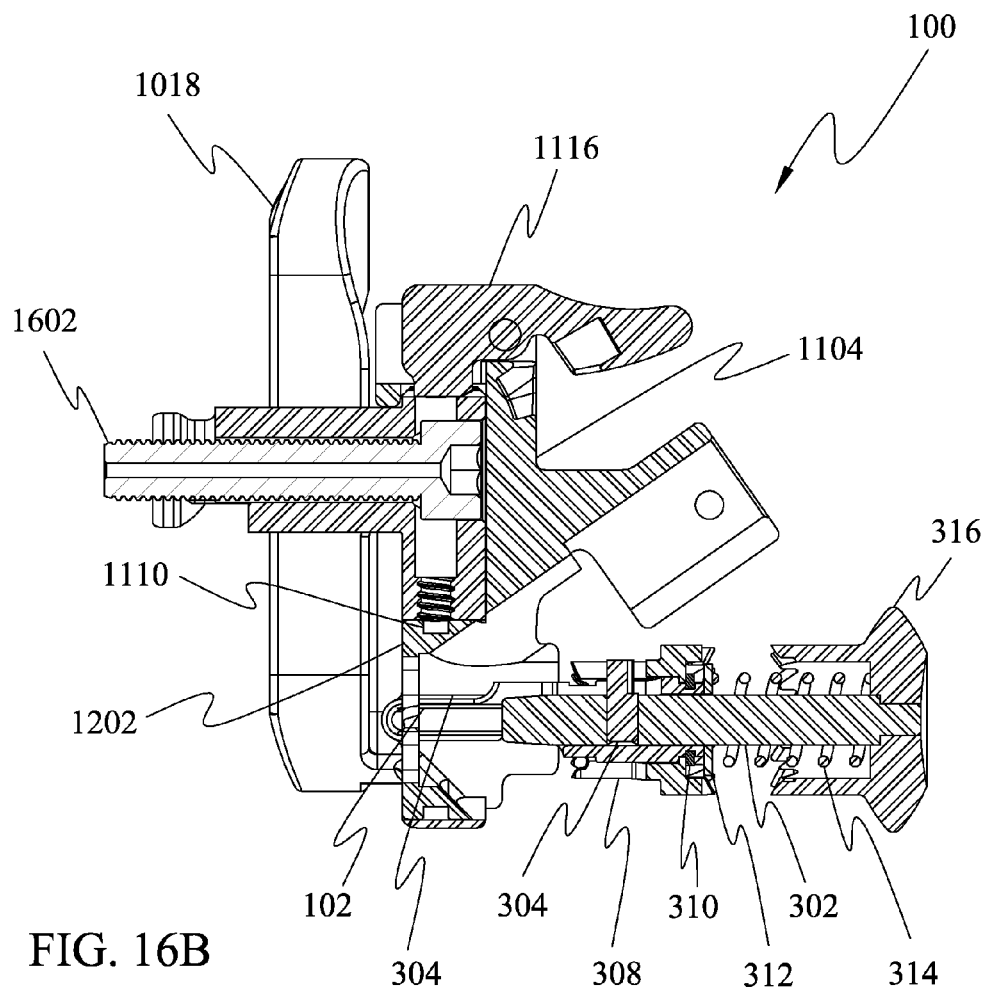
FIG. 16B is a sectional perspective view of the system of FIG. 1F about the axis 16-16.

Each of the arms 910 may define beveled surface 928 that compliment with beveled surface 1101 that may be provided in the cylindrical body 1102 (illustrated in FIG. 11A) of the arm 108. The beveled surfaces of the pivot enabling member 306 may mate with corresponding beveled surfaces of the arm 108, so that the assembly 104 may be held along an axis where such a fit is established, and the longitudinal axis of the shaft is in line with the axis of the first member 116 provided in the device 110.

Figure 10A:
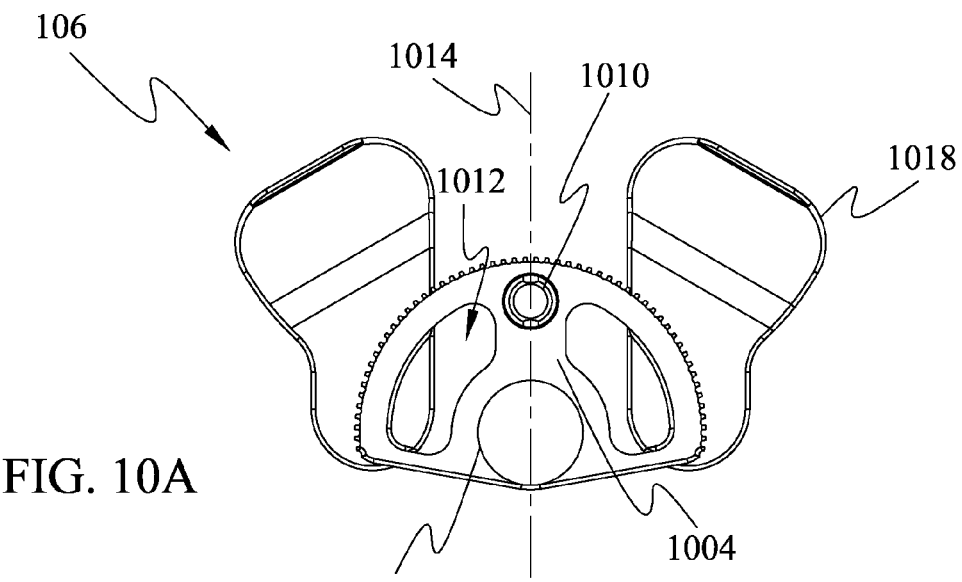
FIG. 10A is a front view of a guide member of the system of FIG. 1F.
Figure 10B:
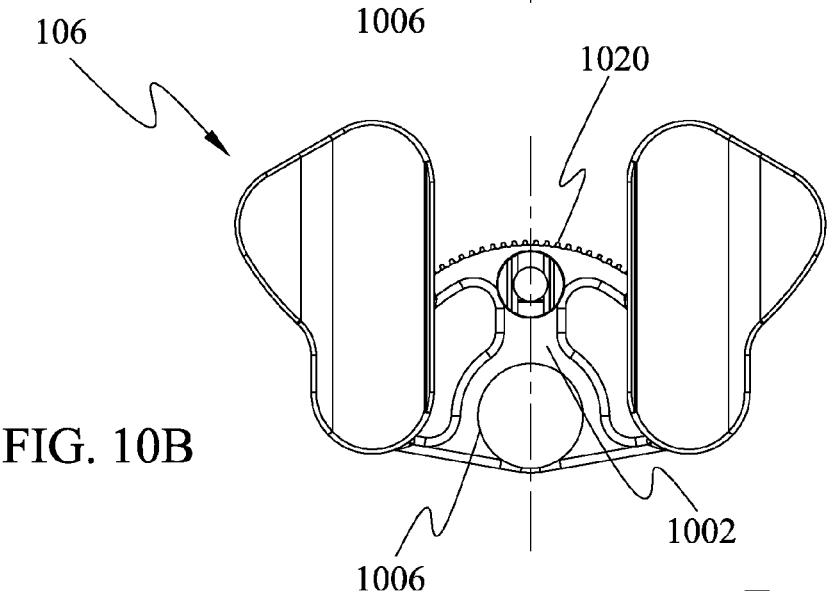
FIG. 10B is a back view of the guide member of the system of FIG. 1F.
Figure 10C:
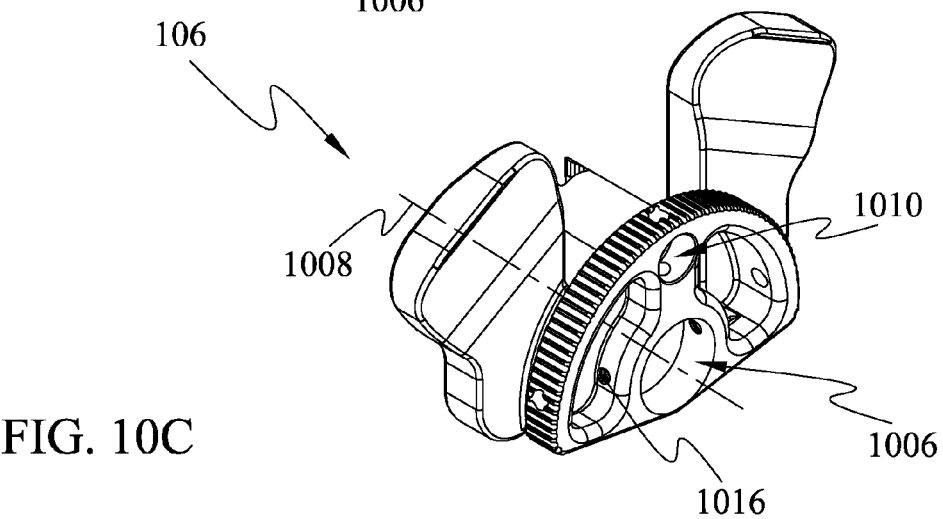
FIG. 10C is a perspective view of the guide member of the system of FIG. 1F.

Referring to FIGS. 10A-10C, the guide member 106 or alignment means may include an arc shaped element. The guide member 106 may include a first surface 1002 and a second surface 1004. The first surface 1002 of the guide member 106 may face the external surface 1802 of the skin 1804, while in use. The second surface 1004 may face away from the external surface 1802 of the skin 1804, when engaged with the device 110. An aperture 1006 (through hole) may be defined in the guide member 106. The aperture 1006 may extend from the first surface 1002 to the second surface 1004. The longitudinal axis 1008 of the aperture 1006 may be referred to as rotational axis 1008. The aperture 1006 may be configured to allow the shaft 302 having the piercing members 102 to translate along the rotation axis 1008 or the longitudinal axis of the shaft 302. The aperture 1006 may be configured to allow the shaft 302 having the piercing members 102 to rotate about the rotation axis 1008.

The guide member 106 may further include an additional aperture 1010, which may enable the system 100 or guide member 106 to be engaged with the device 110 configured to extract hair follicles from underneath the skin 1804.

The guide member 106 may further define a pair of apertures 1012 defined in either sides of a vertical axis 1014 of the apertures 1006. A plurality of holes 1016 extending from the surface defining the aperture 1006 into apertures 1012 and 1010 may be defined. The longitudinal axis of the holes 1016 may be perpendicular to the longitudinal axis of the aperture 1006. Further, a pair of paddles 1018 may be provided in the guide member 106.

The guide member 106 may comprise a plurality of engagement shapes 1020 distributed along the rim of the arc. The engagement shapes 1020 may be configured such that each engagement shape 1020 is equidistant from the rotational axis 1008. Each engagement shape 1020 may be in the form of a groove configured to accommodate a complementing feature.

Referring to FIGS. 11A-12D, the arm 108 may include a cylindrical body 1102, a pillar 1104 and an extending member 1106. The arm 108 may be configured to be operable to at least partially rotate about the rotational axis 1008 of the guide member 106.

The cylindrical body 1102 may have a longitudinal axis 1103 which may coincide with the rotation axis 1008. The cylindrical body 1102 may include a groove 1108 on its external surface, such that the groove 1108 aligns with the holes 1016 of the guide member 106, when assembled. The arm 108 may be engaged with the guide member 106 by means of engagement screws 1110 which may be passed through the holes 1016 defined in the guide member 106, such that a part of the engagement screws 1110 are received by the groove 1108.

The cylindrical body 1102 may define an opening 1112 at one of its ends, so that the shaft 302 may be received through the opening 1112. At a second end of the cylindrical body 1102 a counter pressure device 1202 may be provided.

The inner surface of the cylindrical body 1102 may define beveled surfaces 1101. The beveled surfaces 1101 may coincide with the beveled surfaces 928 provided in the pivot enabling member arms 910. The beveled surfaces 928 and 1101 may mate with each other by means of friction fit, so that the assembly 104 may be coaxial with the first member 116 of the device 110 that may be employed for extracting hair follicle from underneath the external surface 1802 of the skin 1804.

The pillar 1104 may extend from the outer surface of the cylindrical body 1102. The pillar 1104 may extend perpendicularly to the longitudinal axis 1103 of the cylindrical body 1102. The extending member 1106 may extend from the end of the pillar 1104 which may be away from the cylindrical body 1102. The extending member 1106 may define an opening 1107 at the center, such that, two arms 1109 may be defined on each side of the opening. The extending member 1106 may further define a pair of pivot openings 1114 on each of its two arms 1109. The pivot opening 1114 may be defined in the portion of the arms 1109 which may be closer to the pillar 1104.

The arm 108 may further include a latch 1116. The latch 1116 may be shaped to define a handle 1118, a shoulder 1120 and a beak shaped feature 1122. The beak shaped feature 1122 may extend from the shoulder 1120. Inferior to the shoulder 1120, a protruded portion 1124 may be defined. The protruded portion 1124 may compliment the engagement shapes 1020 or grooves provided in the guide member 106. The latch 1116 may define a hole 1128 that may receive a pivot pin, which may facilitate the latch 1116 to pivot about the longitudinal axis of the pivot pin or hole 1128. The latch may further define a spring accommodation hole 1125 configured to receive a spring, such that the spring pushes the latch 1116 into a position that engages the protruded portion 1124 with the guide member 106.

The arm 108 may further include a collar 1126 which may be configured to receive an image capturing system.

The counter pressure device 1202 may be a circular plate with a targeting aperture 1204 at the center of the plate. The counter pressure device 1202 may further define piercing member accommodation opening 1206 defined on both sides of the targeting opening 1204. The piercing members 102 may translate to-and-fro through the piercing member accommodation opening 1206. Further, the piercing member accommodation opening 1206 may define an oblong shape so that the piercing members 102 may pivot while the piercing members 102 have extended through the piercing member accommodation opening 1206 or the counter pressure device 1202.

The counter pressure device 1202 may define a pair of pivot holes 1208. The longitudinal axis of the pivot holes 1208 may be perpendicular to the longitudinal axis of the targeting opening 1204. The pivot holes 1208 may be defined such that a surface 1210 of the counter pressure device 1202 that interfaces with the skin is flush, without protrusions.

The counter pressure device 1202 may apply pressure over or around the tissue comprising hair follicle when it is held against the external surface 1802 of the skin 1804.

Referring to FIGS. 13A-13H, the engagement member 304 may be received in the second aperture 416 defined in the shaft 302. The pivot enabling member 306 may be engaged with the second engagement member 308, such that shoulder 914 presses against a bottom portion of the ring 812 of the second engagement member 308, and the second neck 918 extends over the ring 812. The first ring 310 may be engaged around the second neck 918, thereby preventing the second engagement member 308 from disengaging from the pivot enabling member 306. The second ring 312 may be placed over the head 920 of the pivot enabling member 306. The compression member 314 may be placed over the second ring 312. The proximal end 404 of the shaft 302 may be received through the pivot enabling member 306, second engagement member 308, the first ring 310, the second ring 312, and the compression member 314. The shaft 302 may be engaged with the cap 316, such that the neck 414 of the shaft 302 is received in the aperture 710 defined in the cap 316. The shaft 302 may be engaged with the cap 316, such that relative movement between the shaft 302 and the cap 316 is prevented, once they are engaged together.

Referring to FIG. 14A-F, the piercing members 102 are illustrated in the extended position 1402 in FIG. 14D. In the extended position 1402, the engagement member 304 is received by the extended position lock slot 814. Referring to FIG. 14A, the piercing members 102 are illustrated in the retracted position 1404. In the retracted position 1404, the engagement member 304 is received by the retracted position lock slot 816.

Pressing of the cap 316 may push the shaft 302 in a first direction, for example towards the skin 1804, and may also enable partial rotation of the second engagement member 308, such that the engagement member 304 is aligned with one of a plurality of extended position lock slot 814 defined in the second engagement member 308. Releasing of the cap 316 may enable the shaft 302 to translate in a direction opposite to the direction in which it translated earlier. The translatory movement of the shaft 302 will be stopped by engagement of the engagement member 304 with the second engagement member 308 at the extended position lock slot 814, thereby enabling the piercing members 102 to assume an extended position.

The piercing members 102 may be made to retract out of the tissue from the extended position to a retracted position by pressing the cap 316 again. Pressing of the cap 316 pushes the shaft 302 further, thereby disengaging the engagement member 304 from the second engagement member 308. Pressing of the cap 316 may also enable partial rotation of the second engagement member 308, such that the engagement member 304 is now aligned with one of the retracted position lock slot 816 defined in the second engagement member 308. Releasing of the cap 316 will enable the piercing members 102, along with the shaft 302 to translate out of the tissue. The translatory movement of the shaft 302 may be stopped by engagement of the engagement member 304 with the second engagement member 308 at one of the plurality of retracted position lock slot 816, thereby enabling the piercing members 102 to assume the retracted position.

Referring to FIGS. 15A-16B, the assembly 104 may be engaged with the arm 108. Pivot holes 1208 defined in the arm 108 may be aligned with the apertures 926 defined in the pivot enabling member 306. A pair of pivot pins may be engaged in the apertures 926 and the pivot holes 1208, thereby enabling the assembly 104 to pivot about a pivot axis.

The latch 1116 may be engaged to the arm 108. A pivot pin 1502 (FIG. 11B) may be passed through the pivot hole 1128 defined in the latch 312 and the pair of pivot openings 1114 defined in the extending member 1106, thereby enabling the latch 1116 to pivot.

The arm 108 may be engaged to the guide member 106. Engagement screws 1110 may be passed through the holes 1016 defined in the guide member 106, such that a portion of the engagement screws 1110 extend into the groove 1108 defined in the arm 108, thereby engaging the arm 108 with the guide member 106, while allowing the arm 108 to rotate.

The guide member 106 may be engaged with a device which may be used to extract hair follicles from beneath the external surface of the skin. The additional aperture 1010 defined in the guide member 106 may allow an engagement screw 1602 to engage the guide member 106 with the device.

Figure 17A:
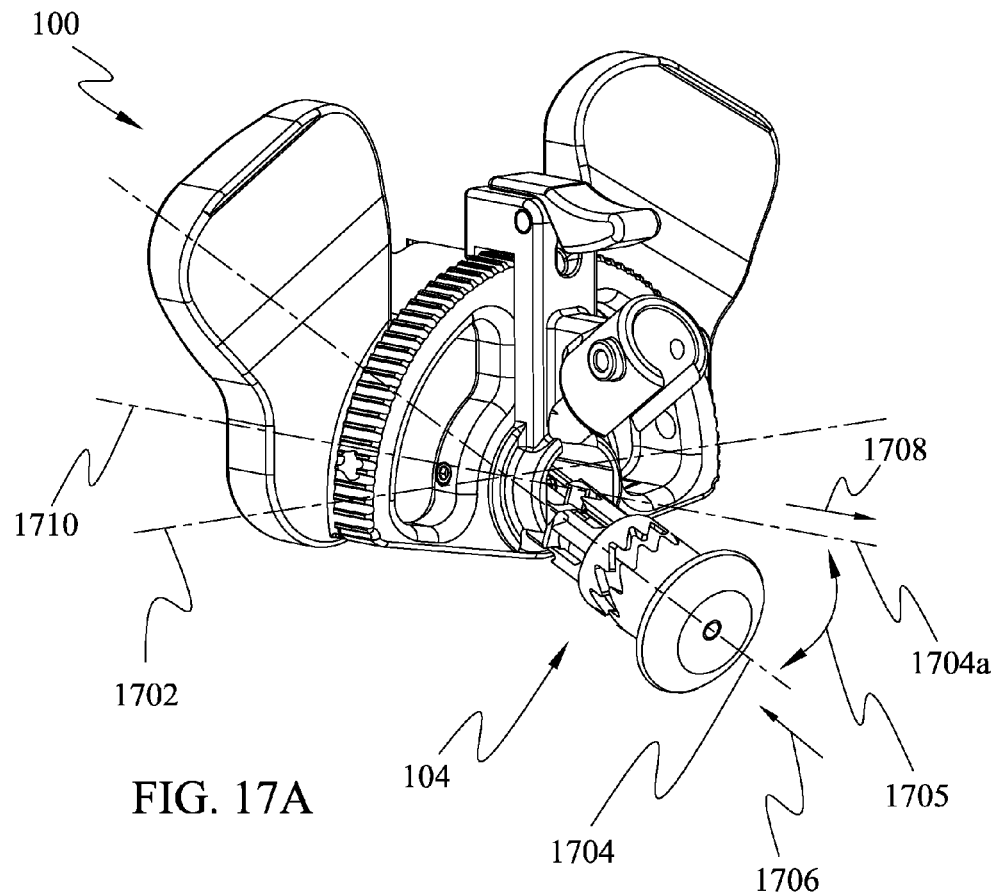
FIGS. 17A-17C are perspective views of the system of FIG. 1F.
Figure 17B:
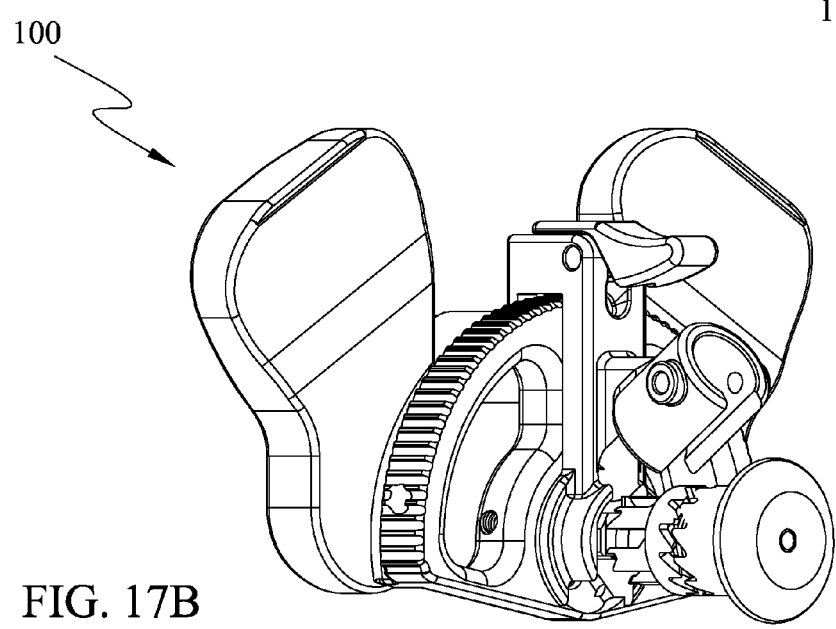
Figure 17C:
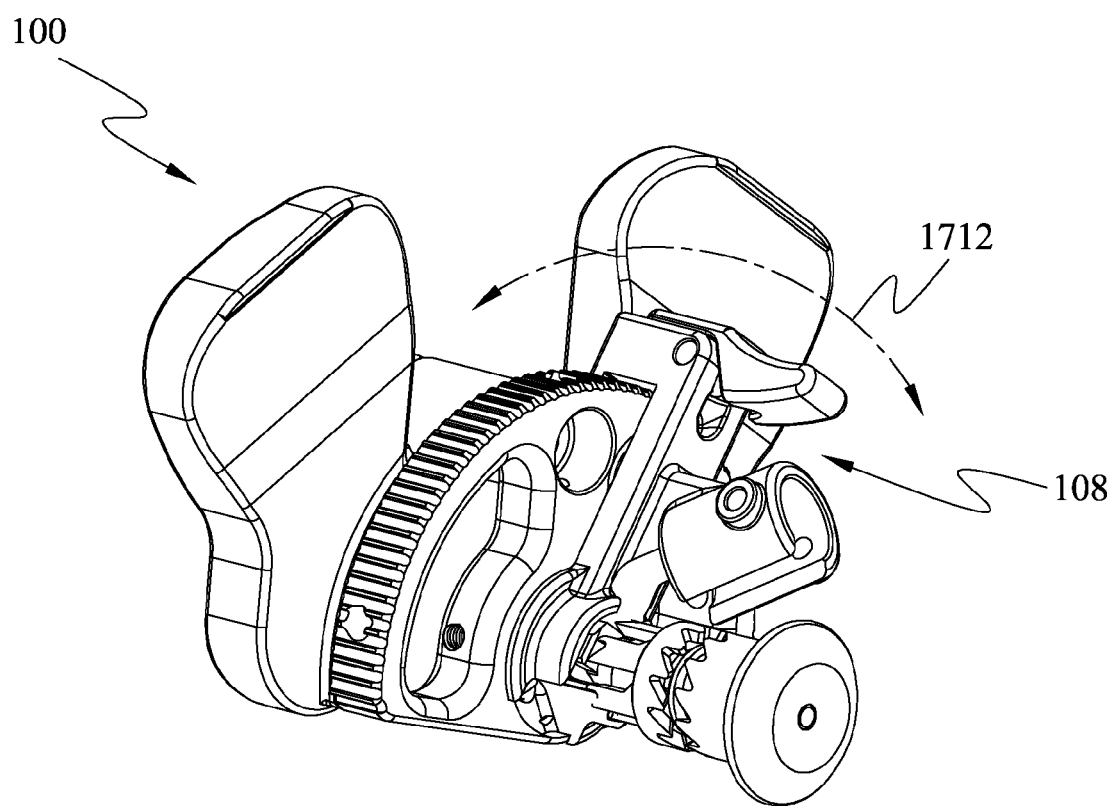
Figure 18A:
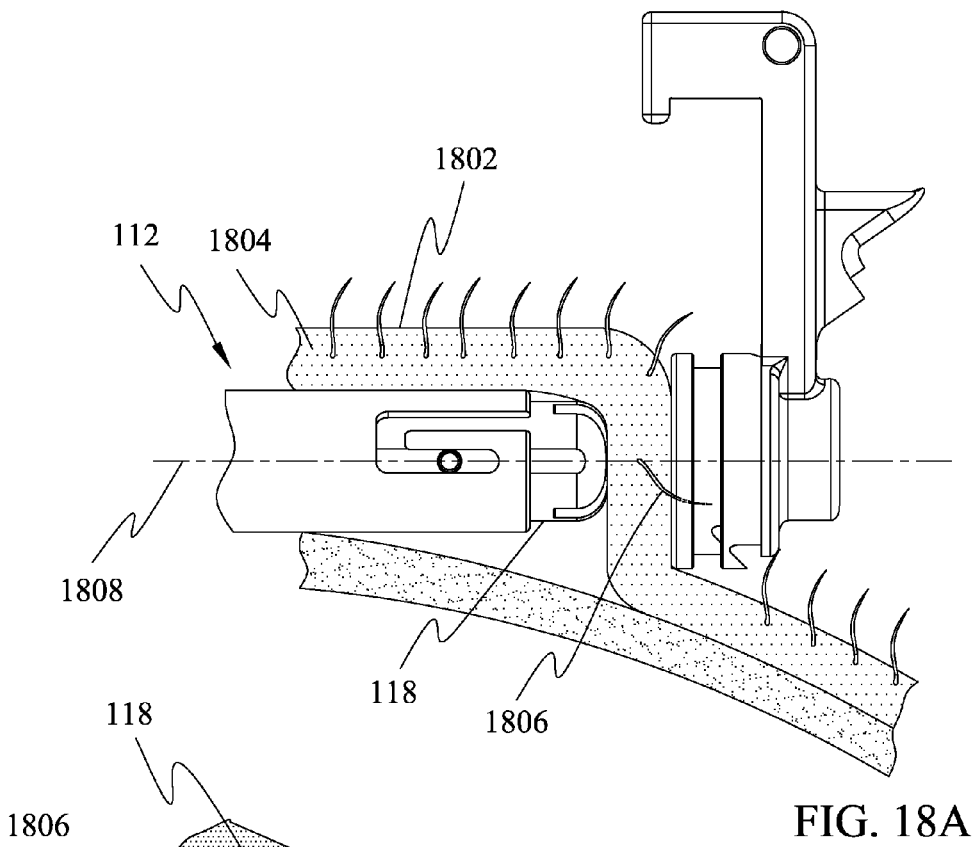
FIGS. 18A-18F are perspective views illustrating altering an alignment and extraction of a hair follicle.
Figure 18B:
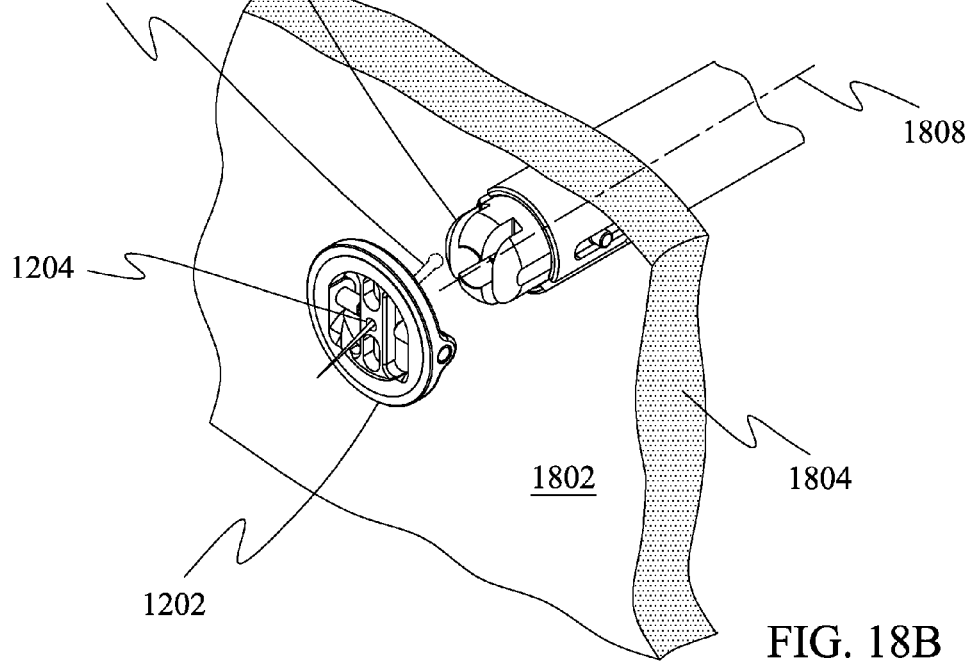
Figure 18C:
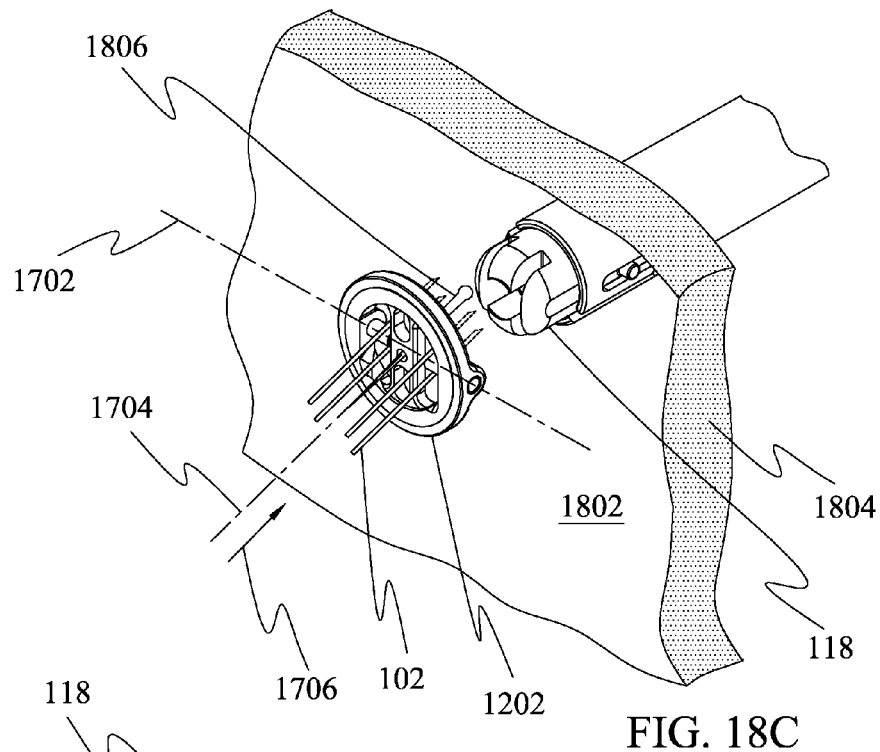
Figure 18D:
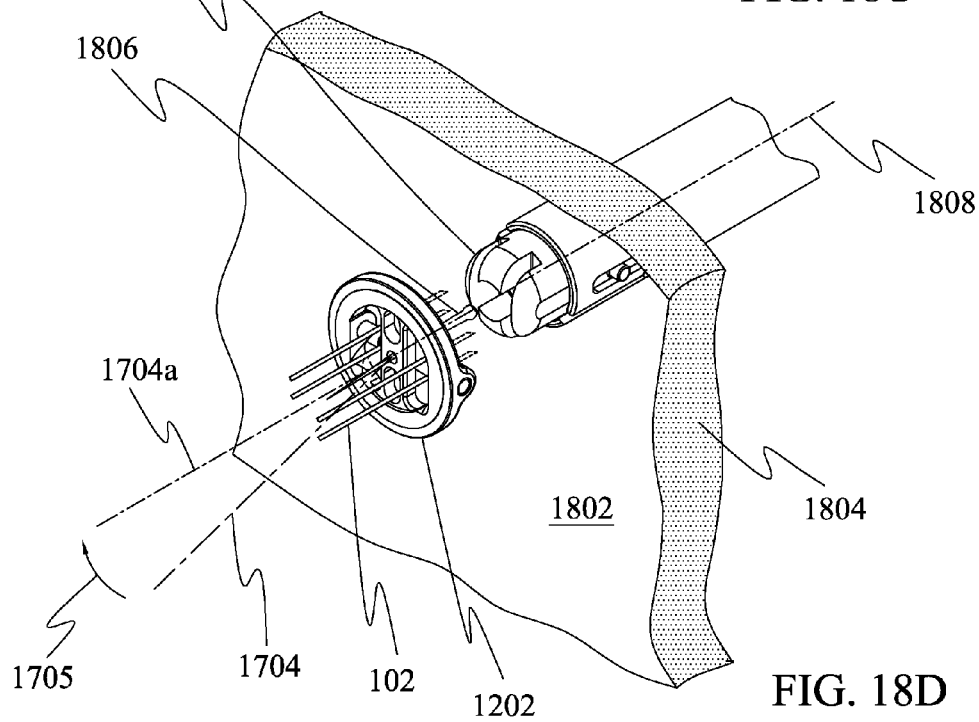
Figure 18E:
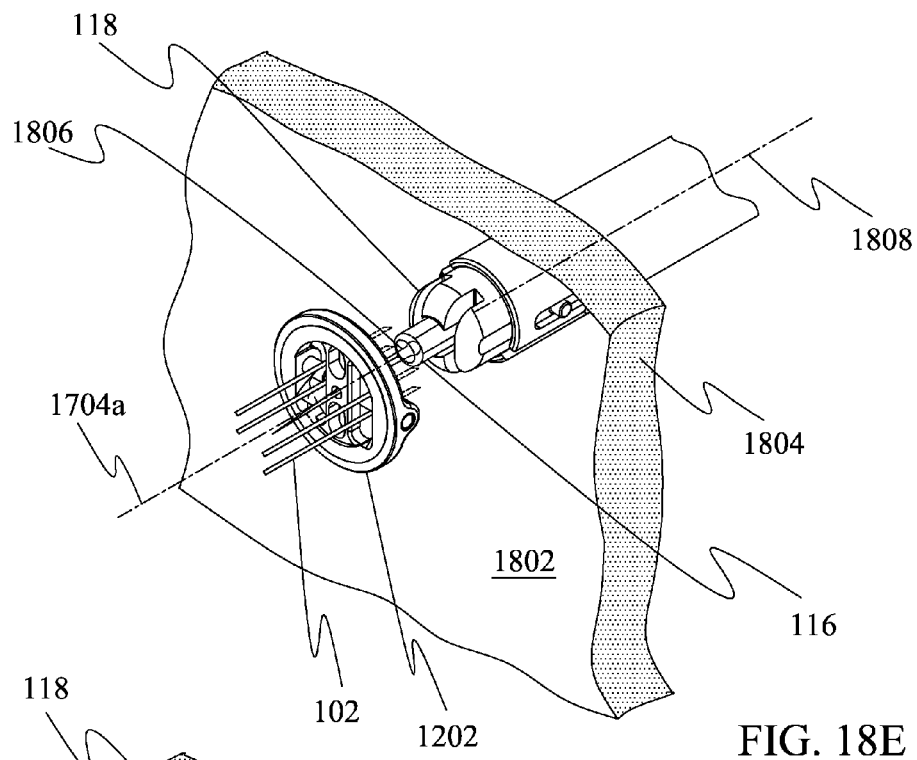
Figure 18F:
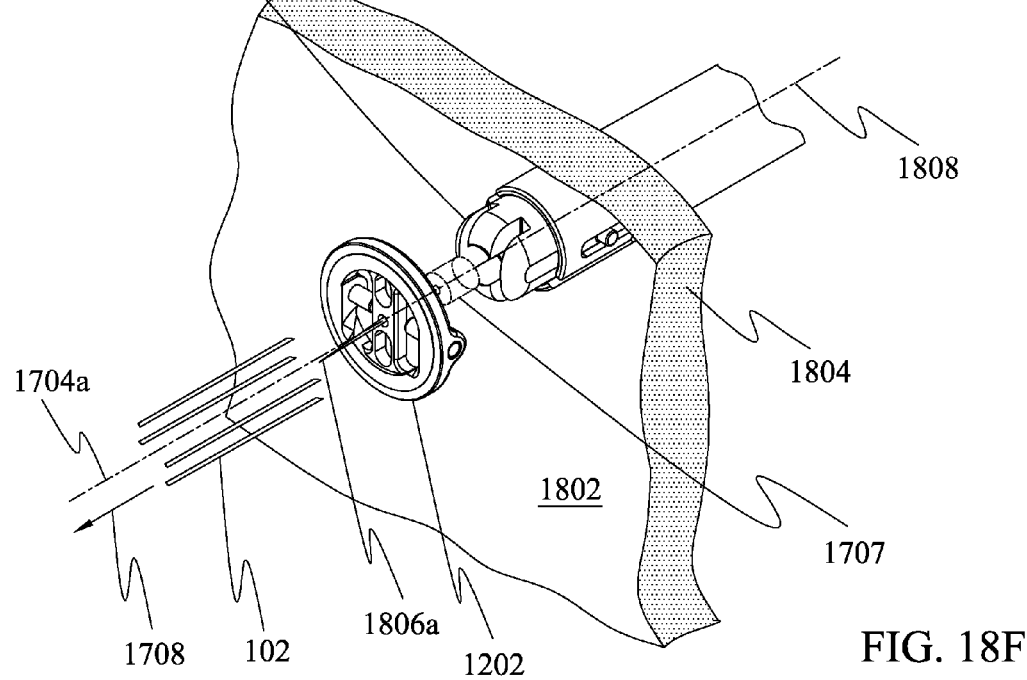

Referring to FIGS. 17A-17C, the system 100 may include a pivot axis 1702 such that the assembly 104 may pivot about the pivot axis 1702. Pivoting the assembly 104 about the pivot axis allows the piercing member 102 to pivot about the pivot axis 1702.

The assembly 104 may be pivoted as indicated by the arrow 1705 to choose a first chosen axis 1704. The piercing member 102 may be configured to translate along the first chosen axis 1704 in a first direction 1706. The translation of the piercing member 102 along the first chosen axis 1704 in the first direction 1706 may allow the piercing member 102 to pierce through the external surface 1802 of the skin 1804. The first chosen axis 1704 may be chosen by pivoting the assembly 104. The assembly 104 may be pivoted so that the shaft 302 or piercing members 102 may be aligned with a second chosen axis 1704a. The piercing member 102 may be configured to translate along the second chosen axis 1704a in a second direction 1708. The translation of the piercing member 102 along the second chosen axis 1704a in the second direction 1708 may allow the piercing member 102 to retract out of the skin. The pivot axis 1702 may intersect with the first and second chosen axis 1704, 1704a. The piercing member 102 may be configured to translate along the first chosen axis 1704 in the first direction 1706 to assume an extended position 1402. The piercing member 102 may be configured to translate along the second chosen axis 1704a in the second direction 1708 to assume a retracted position 1404.

The system 100 may further include a rotational axis 1710. The piercing member 102 may be configured to rotate as indicated by arrow 1712 about the rotational axis. The pivot axis 1702 may intersect the rotational axis. The chosen axis along which the piercing member 102 retracts out of the skin may be the rotational axis. The arm 108 may be configured to rotate at least partially about the rotational axis 1710. The rotation of the arm 108 about the rotational axis may allow the piercing members 102 to rotate about the rotational axis. The rotational axis may intersect the pivot axis 1702. The arm 108 may be configured to rotate about the rotational axis in either direction from a central position.

The grooved engagement shapes 1020 may engage with the protruded portion 1124 provided at the tip of the beak shaped feature 1122 of the arm 108 thereby allowing the arm 108 to rotate about the engagement shapes 1020 and be locked at a desired position. The rotation of the piercing member 102 may enable the piercing members 102 to align with at least a hair follicle that may have a complex or compound angle.

Referring to FIGS. 1C-1E and 18A-18F, the system 100 may be used in conjunction with the device 110. The device 110 may be employed to extract hair follicles from underneath the external surface 1802 of the skin 1804.

A portion 112 of the device 110 may be configured to enter an area beneath the external surface 1802 of the skin 1804 towards the donor region 114. An incision 120 may be made close to the donor region 114. The incision 120 provides access to the portion 112 of the device 112 to be inserted underneath the skin 1804, thereby providing access to hair follicles from underneath the external surface 1802 of the skin 1804.

The first member 116 may include a cutting tip towards its end. The first member 116 may be configured to rotate about a longitudinal axis 1808 such that the rotation may enable the first member 116 to cut through a tissue that may have the target hair follicle 1806. A second member may operate in conjunction with the first member 116 which may enable the device 110 to clip the hair follicles 1806 which may have been cut by the first member 116.

The tissue stabilizing member 118 may be configured to apply pressure against or around a tissue comprising a hair follicle 1806 from underneath the external surface 1802 of the skin 1804. Once the tissue comprising the target hair follicle 1806 may be stabilized and prepared for extraction, the first member 116 may translate along its longitudinal axis to cut the tissue by rotating about its longitudinal axis.

The guide member 106 may be held against the external surface 1802 of the skin 1804. While holding the guide member 106 against the external surface of the skin, the counter pressure device 1202 may apply pressure over or around the tissue comprising the hair follicle 1806. The region around which the counter pressure device 1202 operates may be the external surface 1802 of the region around which the tissue stabilizing member 118 operates from underneath the skin 1804. The tissue comprising the target hair follicle 1806 may be disposed between the tissue stabilizing member 118 and the counter pressure device 1202.

The hair follicle 1806 to be extracted may be seen through the target aperture 1204 provided in the counter pressure device 1202. The hair follicle 1806 may be misaligned with respect to the first member 116 or the tissue stabilizing member 118. If the first member 116 were to cut through the tissue to extract the hair follicle 1806 when it is misaligned, then the hair follicle might be transected, which is not desirable. Hence, aligning the hair follicle 1806 with the axis of the first member 116 may be desired.

In order to align the hair follicle 1806 with the first member 116, the piercing member 102 may be rotated about the rotational axis depending on the alignment of the hair follicle 1806. The piercing members 102 may be pivoted about the pivot axis so that the axis of the piercing members 102 may be parallel, or the axis of the shaft 302 carrying the piercing members 102 is in line, with the axis of the hair follicle 1806.

After aligning the piercing members 102, the piercing members 102 may be translated into the skin in the first direction 1706 along the first chosen axis 1704. Thereafter, the piercing members 102 may pivoted as indicated by the arrow 1705 about the pivot axis 1702 such that pivoting the piercing members 102 may cause the hair follicle 1806 disposed between the piercing members 102 to pivot. Pivoting the piercing members 102 may be required to align the hair follicle 1806 disposed between the piercing members 102 with the longitudinal axis 1808 of the first member 116 of the device 110. Once the axis of the hair follicle 1806 is aligned with the longitudinal axis 1808 of the first member 116, the first member 116 of the device 110 may be operated to cut the hair follicle 1806. The second member may be operated to clip the hair follicles 1806 cut by the first member 116. Once the extraction of the hair follicle 1806 may be completed, the first member 116 and the second member may translate in a direction away from the external surface 1802, leaving behind a wound 1707 in the skin 1804, without causing any wound on the external surface 1802. The piercing members 102 may be retracted out of the skin 1804 along the second chosen axis 1704a in the second direction 1708. The second chosen axis 1704 a may be in line or parallel to the longitudinal axis of the first member 116.

Figure 19:
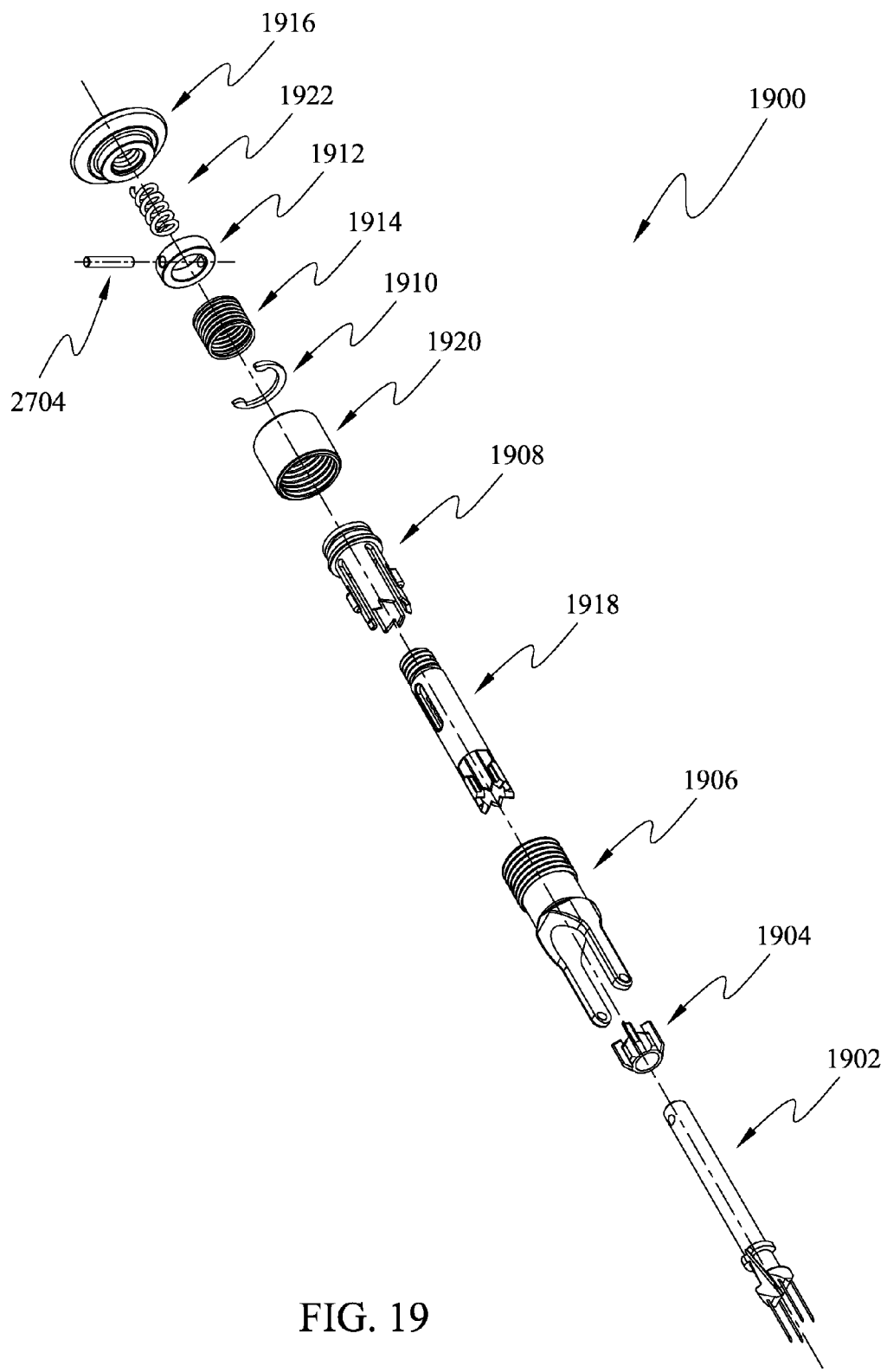
FIG. 19 is an exploded perspective view of an assembly.

Referring to FIG. 19, an assembly 1900 may include a shaft 1902, an engagement member 1904, a pivot enabling member 1906, a second engagement member 1908, a first ring 1910, a second ring 1912, a compression member 1914 and a cap 1916, an indexer 1918, a knob 1920 and a second compression member 1922.

Figure 20:
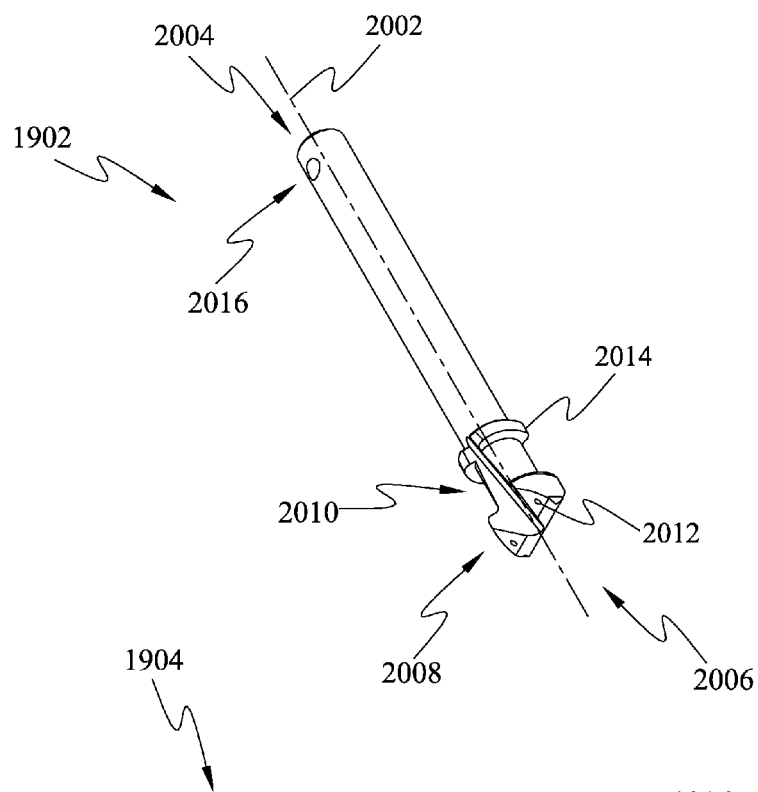
FIG. 20 is a perspective view of a shaft of the assembly of FIG. 19.

Referring to FIG. 20, the shaft 1902 may have portion that has a cylindrical cross section along its longitudinal axis 2002. The shaft 1902 may include a proximal end 2004 and a distal end 2006. The shaft 1902 may include a base 2008 at the distal end that may have a polygonal cross section. The base 2008 has a V shaped groove, which may enable a targeting system such as a microscope to capture image of hair extending out of a targeting aperture which may be provided in the counter pressure device 1202. The width of the base 2008 may be greater than the diameter or width of rest of the portion of the shaft 1902. One of the surfaces of the base 2008 may define a groove 2010.

The base 2008 of the shaft 1902 may include a plurality of first apertures 2012 extending from the distal end 2006 into the shaft 1902 parallel to the longitudinal axis 2002 of the shaft 1902. The first apertures 2012 may be configured to accommodate the piercing members 102 such that a portion of the piercing members 102 may be accommodated in the first apertures 2012, and a remaining portion which includes the pointed distal end 204 protrudes out of the shaft 1902.

The shaft 1902 may define a shoulder 2014. The shoulder 2014 may have a circular cross section such that the shoulder 2014 may have a larger diameter than the diameter of a portion the shaft 1902, immediately succeeding the shoulder 2014 towards the proximal end 2004. The shaft 1902 may further define a through hole 2016 towards the proximal end 2004. The through hole 2016 may be perpendicular to the longitudinal axis 2002 of the shaft 1902

Figure 21:
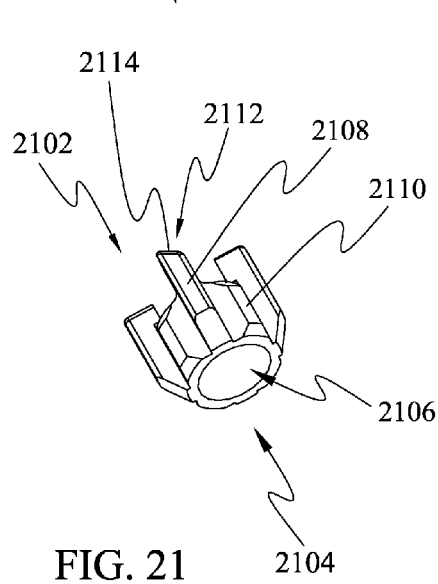
FIG. 21 is a perspective view of an engagement member of the assembly of FIG. 19.

Referring to FIG. 21, the engagement member 1904 may have a proximal end 2102 and a distal end 2104. The engagement member 1904 may define a through hole 2106 extending from the proximal end 2102 until the distal end 2106. The through hole 2106 may be configured to receive the shaft 1902, such that the engagement member 1904 rests over the shoulder 2014 of the shaft 1902.

The engagement member 1904 may define a plurality of laterally extending projection portions 2108 spread around the through hole 2106. An intermediate portion 2110 may be present between adjacent projection portions 2108. Outer diameter of the engagement member 1904 measured at the intermediate portions 2110 may be smaller than the outer diameter of the engagement member 1904 measured at the projection portions 2108. The outer diameter of the inner diameter of the second engagement member 1908 measured at the second engagement member arms 2408.

Each projection portion 2108 may define a tooth 2112 facing the proximal end 2102. The tooth 2112 may define an asymmetrical "V" or "U" shaped configuration. Each tooth 2112 may have a beveled surface 2114. The inclination of the beveled surface 2114 may be such that, force acting on the beveled surface 2114 may enable rotation of the engagement member 1904.

Figure 22:
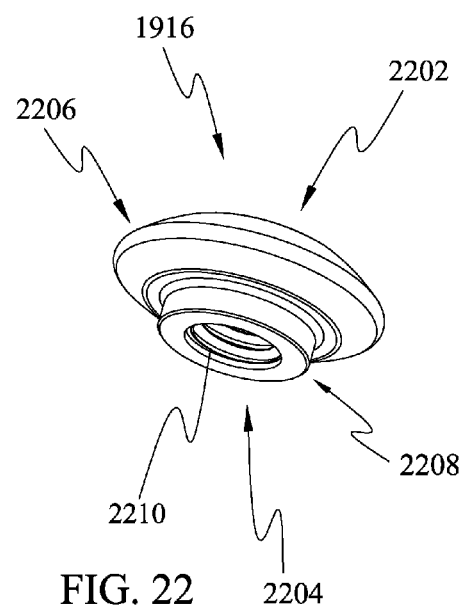
FIG. 22 is a perspective view of a cap of the assembly of FIG. 19.

Referring to FIG. 22, the cap 1916 may be configured to be engaged with the indexer 1918. The cap 1916 may include a proximal end 2202 and a distal end 2204. The cap 1916 may include a lid portion 2206 and a cover portion 2208. The lid portion 2206 may be provided towards the proximal end 2202 of the cap 1916. The cover portion 2208 may extend from the lid portion 2206 towards the distal end 2204. The cap 1916 may define a threaded hole 2210 that may facilitate engagement of the indexer 1918 with the cap 1916.

Figure 23:
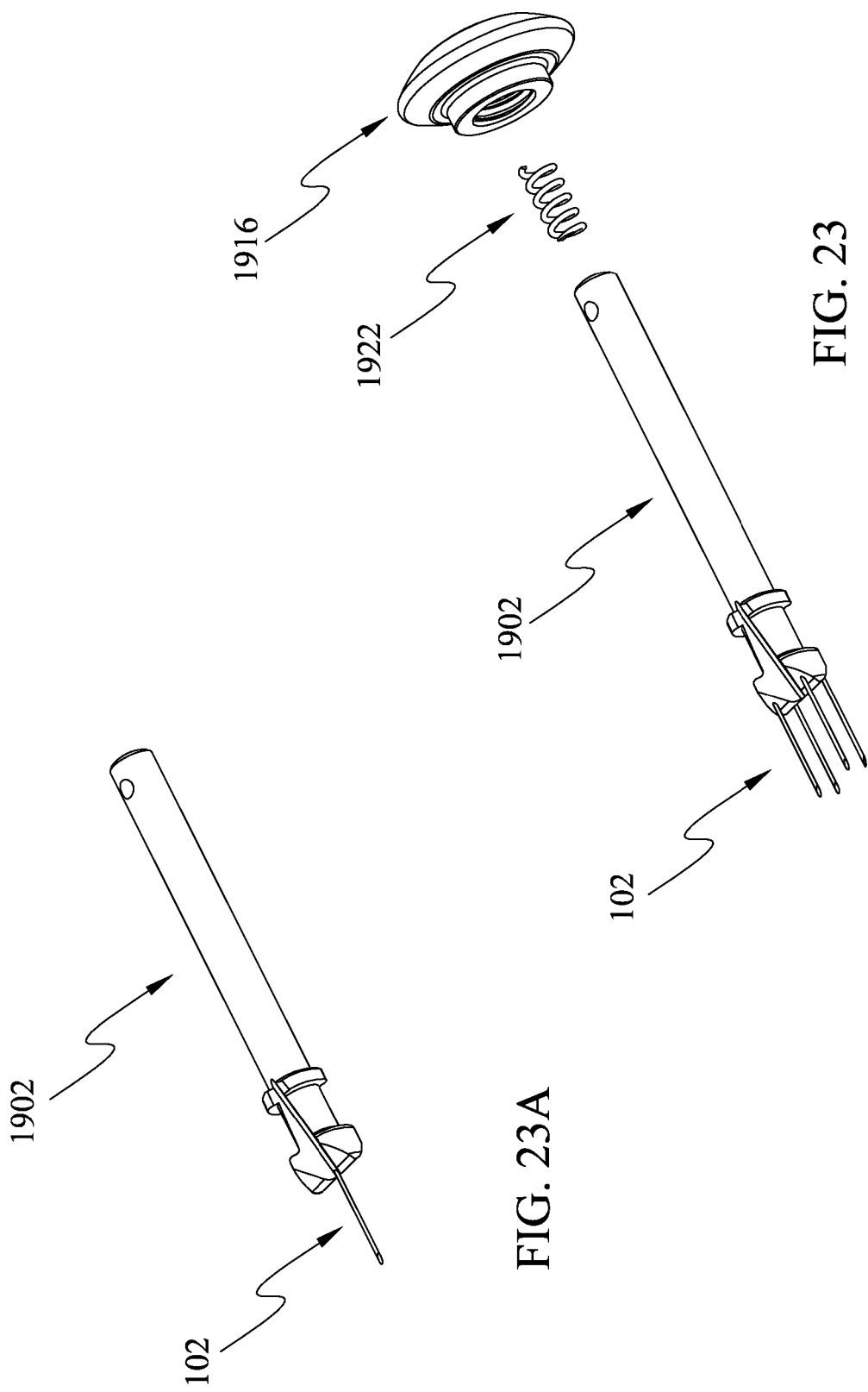
FIG. 23 is an exploded perspective view of the cap, a second compression member and the shaft of the assembly of FIG. 19.

Referring to FIG. 23, the second compression member 1922 may be received by the indexer 1918, such that the second compression member 1922 may be disposed between the proximal end 2004 of the shaft 1902 and the lid 2206 of the cap 1916.

In FIG. 23, the shaft 1902 as illustrated is adapted with four piercing member 102. The shaft 1902 may be alternatively adapted with a single piercing member 102 (refer FIG. 23A). The single piercing member 102 may be disposed along the longitudinal axis or the longitudinal center of the shaft 1902. Alternatively, the single piercing member 102 may be offset from the longitudinal axis or the longitudinal center of the shaft 1902. In an embodiment, the shaft may be configured to be adapted with more than one piercing member.

Figure 24:
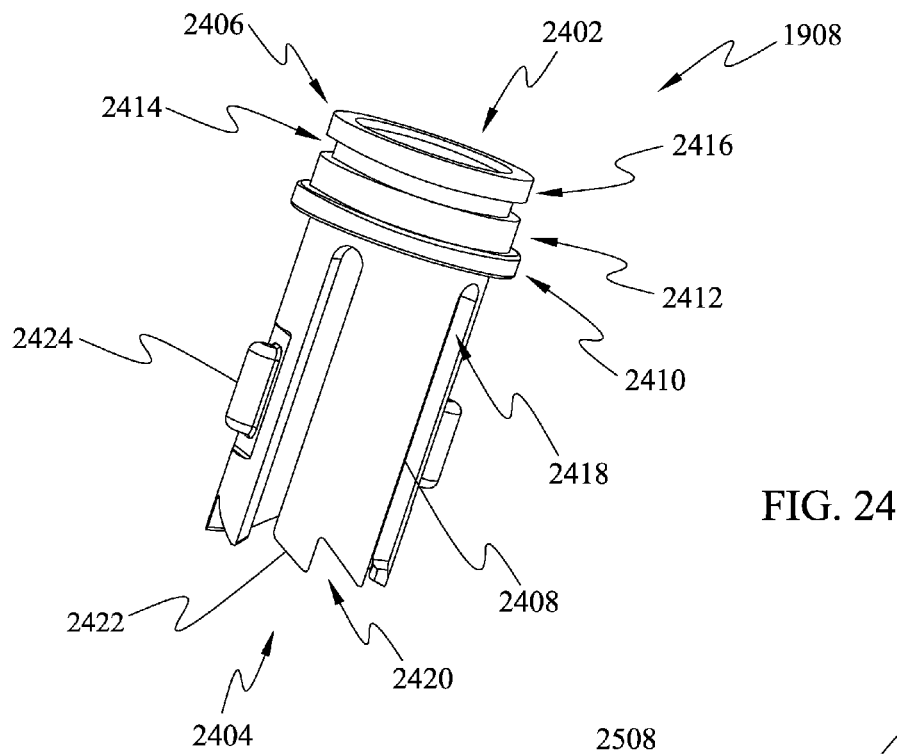
FIG. 24 is a perspective view of a second engagement member of the assembly of FIG. 19.

Referring to FIG. 24, the second engagement member 1908 may include a proximal end 2402 and a distal end 2404. The second engagement member 1908 may include a second engagement member head 2406 towards the proximal end 2402. The second engagement member 1908 may include a plurality of second engagement member arms 2408. The second engagement member arms 2408 may extend from the head 2406 towards the distal end 2404 of the second engagement member 1908.

The second engagement member head 2406 may include a shoulder 2410, a first neck 2412, a second neck 2414 and a second head 2416. The shoulder 2410 may have an outside diameter that may be greater than the outside diameter of adjoining portion of the second engagement member 1908 towards the distal end 2404. The first neck 2412 may have an outside diameter that may be smaller than the outside diameter of the shoulder 2410. The second neck 2414 may have an outside diameter that may be smaller than the outside diameter of the first neck 2412. The second head 2416 may have an outside diameter that may be larger than the outside diameter of the second neck 2414.

The second engagement member arms 2408 may extend in a second direction towards the distal end 2404 from the shoulder 2410. A through slot or retracted position lock slot 2418 may be defined between adjacent second engagement member arms 2408.

Each second engagement member arms 2408 may define an extended position lock slot 2420. Each of the extended position lock slot 2420 may define a shape that may be complimentary to the shape of the tooth 2112 defined by projection portion 2108 of the engagement member 1904.

Each second engagement member arms 2408 may define rotation enabling surface 2422 adjacent to the extended position lock slot 2420. The rotation enabling surface 2422 may be a beveled surface configured such that a member pressed against the rotation enabling surface 2422 may slide into the retracted position lock slot 2418.

The outer surface of two diametrically opposing second engagement member arms 2408 may define protruded features 2424. The protruded features 2424 may have the cross section of a half cylinder. The protruded features 2424 may be configured such that they engage with complimentary feature provided in the pivot enabling member 1906.

Figure 25:
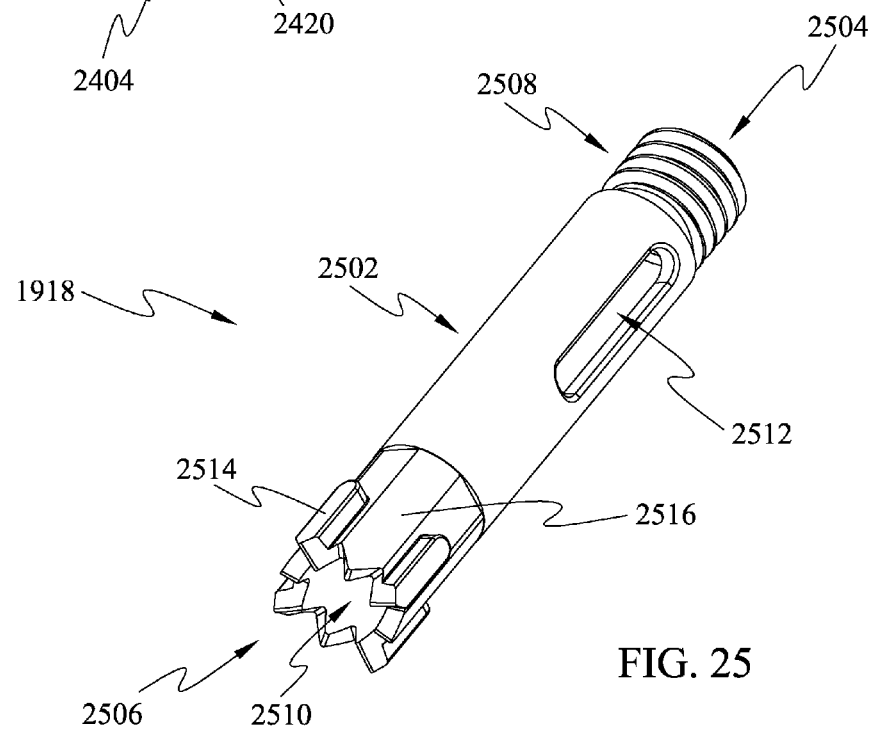
FIG. 25 is a perspective view of an indexer of the assembly of FIG. 19.

Referring to FIG. 25, the indexer 1918 may have a cylindrical body 2502 comprising a proximal end 2504 and a distal end 2506. The proximal end of the cylindrical body 2502 may include a neck 2508, which may be threaded. The neck 2508 may be configured to be received by the threaded portion 2210 of the cap 1916.

The body 2502 of the indexer 1918 may define a hole 2510 which may be configured to receive the shaft 1902. While receiving the shaft 1902, the second compression member 1922 may be received inside the threaded neck 2508 of the indexer 1918. The body 2502 of the indexer 1918 may define through slots 2512 that may be diametrically opposing.

The body 2502 of the indexer 1918 may define a plurality of first indexing teeth 2514 and second indexing tooth 2516. Each of the first indexing teeth 2514 may be present between adjacent second indexing teeth 2516. The outer diameter of the indexer 1918 measured at the first indexing tooth 2514 may be larger than the outer diameter of the indexer 1918 measured at the second indexing tooth 2516. Each of the first indexing teeth 2514 may be in the form of a protrusion.

Figure 26:
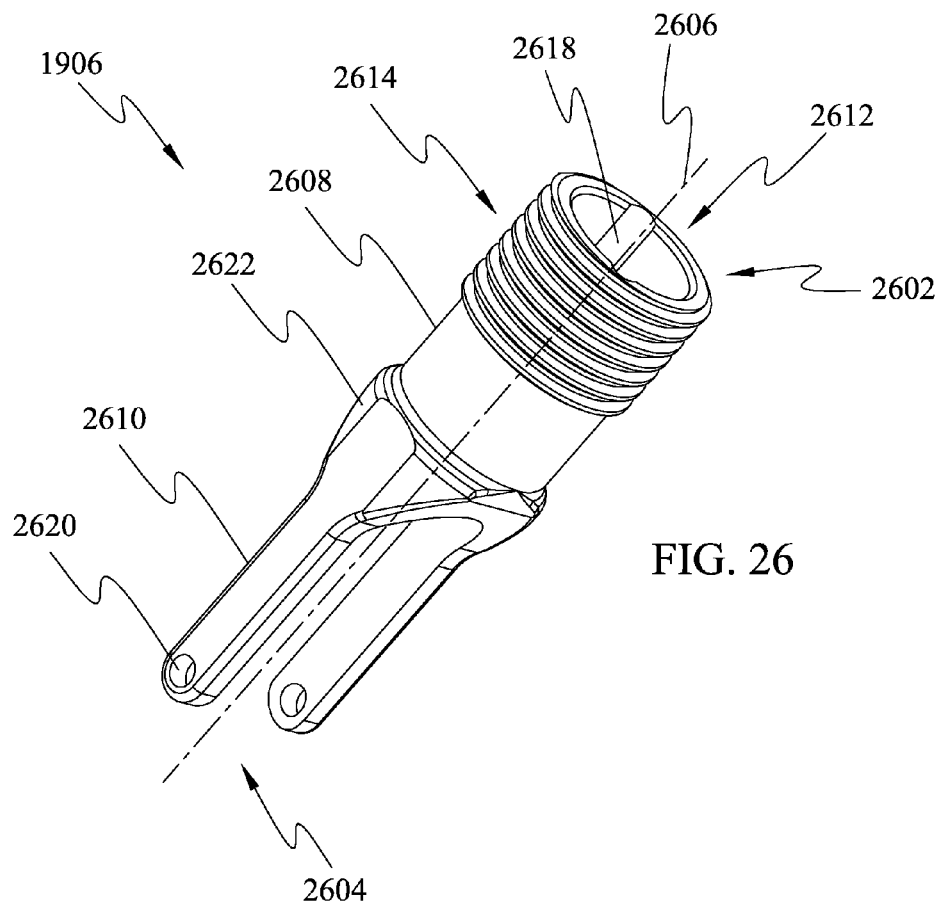
FIG. 26 is a perspective view of a pivot enabling member of the assembly of FIG. 19.

Referring to FIG. 26, the pivot enabling member 1906 may have a proximal end 2602, a distal end 2604 and a longitudinal axis 2606. The pivot enabling member 1906 may include a pivot enabling member head 2608 and a pair of pivot enabling member arms 2610. The head 2608 may define a through hole 2612 configured to allow the shaft 1902 to translate along the axis 2606. A portion of the pivot enabling member head 2608 may include threads 2614 that may engage with complimentary threads 2802 provided in the knob 1920. The pivot enabling member 1906 may define protruded feature receiving slots 2618 in the inner surface of the pivot enabling member head 2608. The protruded feature receiving slots 2618 may be configured to receive protruded features 2424 defined in the second engagement member arms 2408.

The pivot enabling member arms 2610 extend from the pivot enabling member head 2608 towards the distal end 2604. Each of the arms 2610 may define apertures 2620 configured to engage with pivot pins, thereby enabling the pivot enabling member 1906 to pivot.

Each of the arms 2610 may be define a beveled surface 2622 configured to mate and fit with the beveled surface 1101 provided in the cylindrical body 1102 of the arm 108.

The first ring 1910, which may be a retaining ring, may be engaged with the second neck 2414 of the second engagement member 1908. The second ring 1912 may be disposed on top of the compression member 1914. The second ring 1912 may define a through hole which may align with the through hole 2016 defined in the shaft 1902. The second ring 1912 and the shaft 1902 may be engaged by means of a pin 2704 that may be passed through the through holes defined in the second ring 1912 and the through holes 2016 defined in the shaft 1902.

Figure 27:
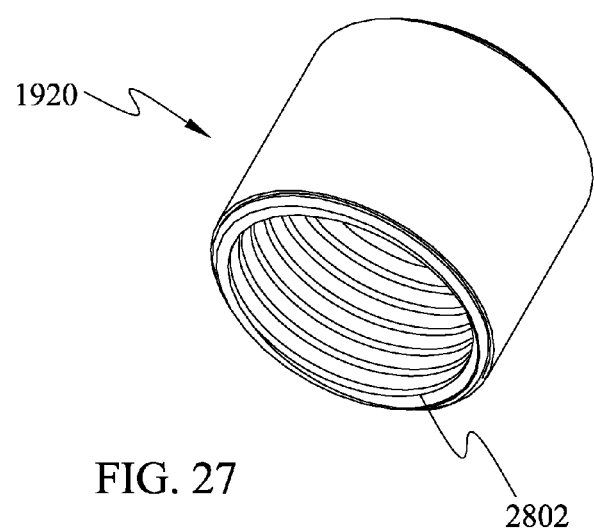
FIG. 27 is a perspective view of a knob of the assembly of FIG. 19.

Referring to FIG. 27, the knob 1920 may be configured to engaged with the pivot enabling member 1906. The inner surface of the knob 1920 may have threads 2802 to enable engagement with the pivot enabling member 1906. The knob 1920 may be configured such that it encircles the shaft 1902 and is positioned between the proximal end 2004 and distal end 2006 of the shaft 1902.

Figure 28A:
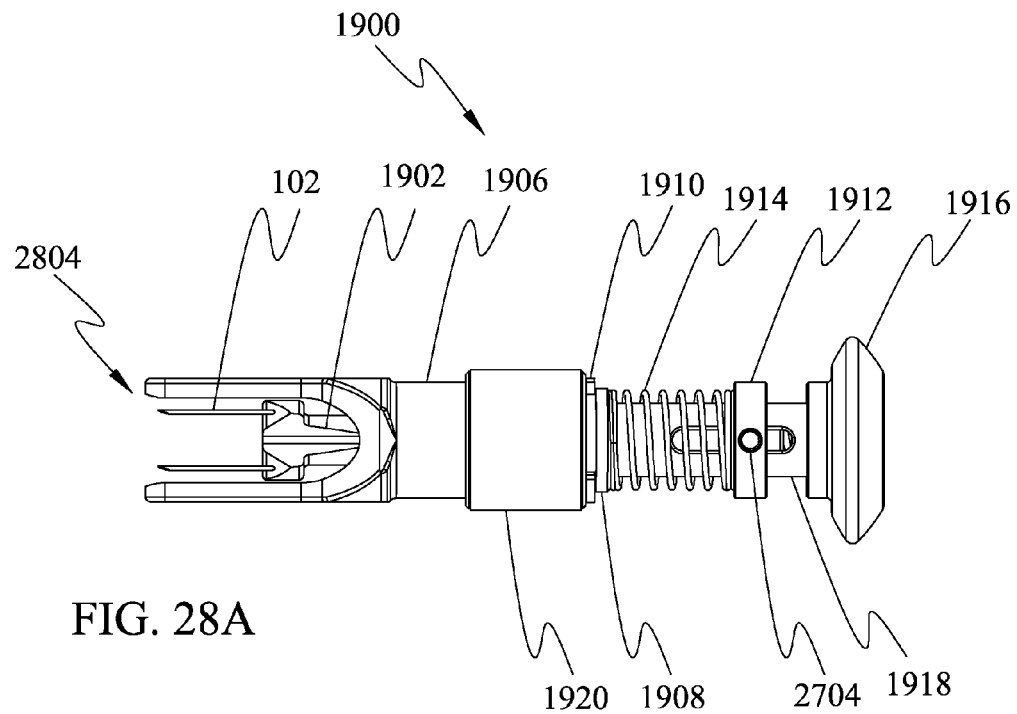
FIGS. 28A-28B are side view illustrating working of the knob of the assembly of FIG. 19.
Figure 28B:
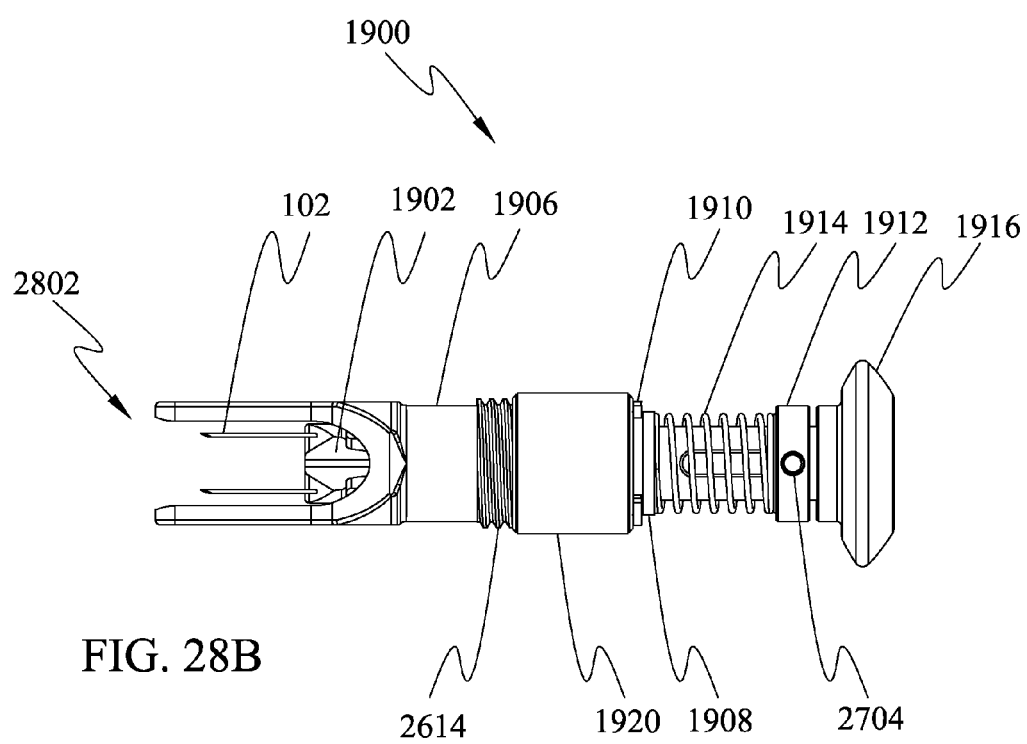
Figure 29G:
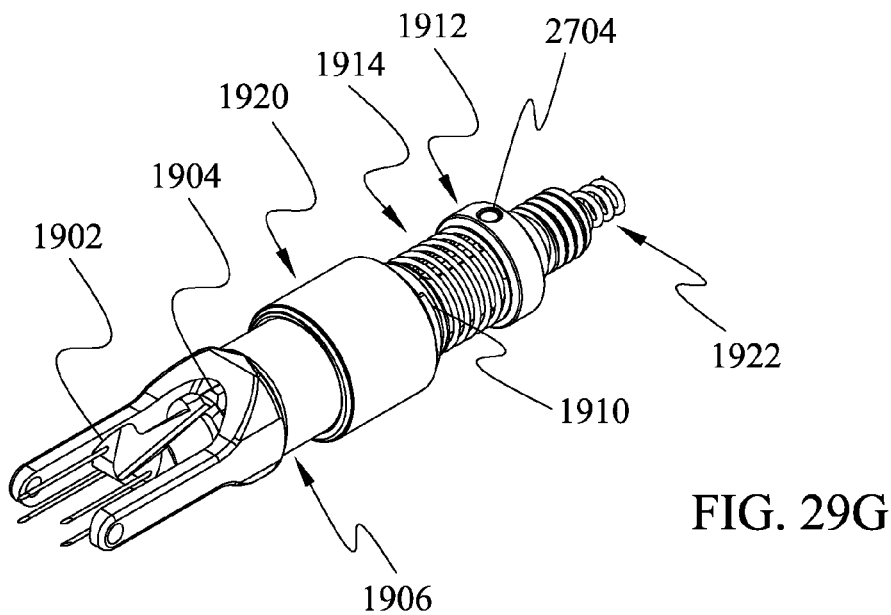
Figure 29H:
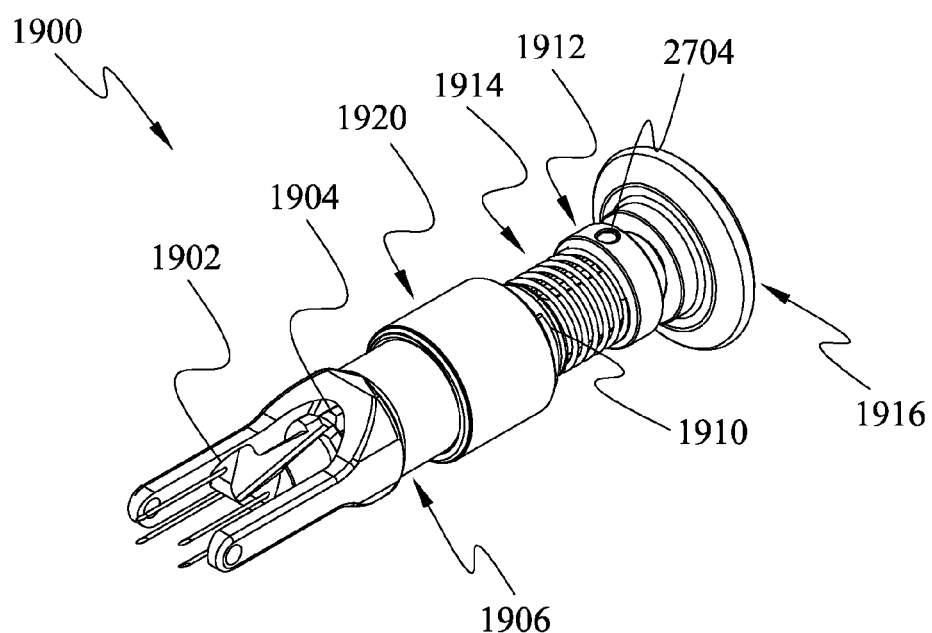
Figures 29I, 29J:
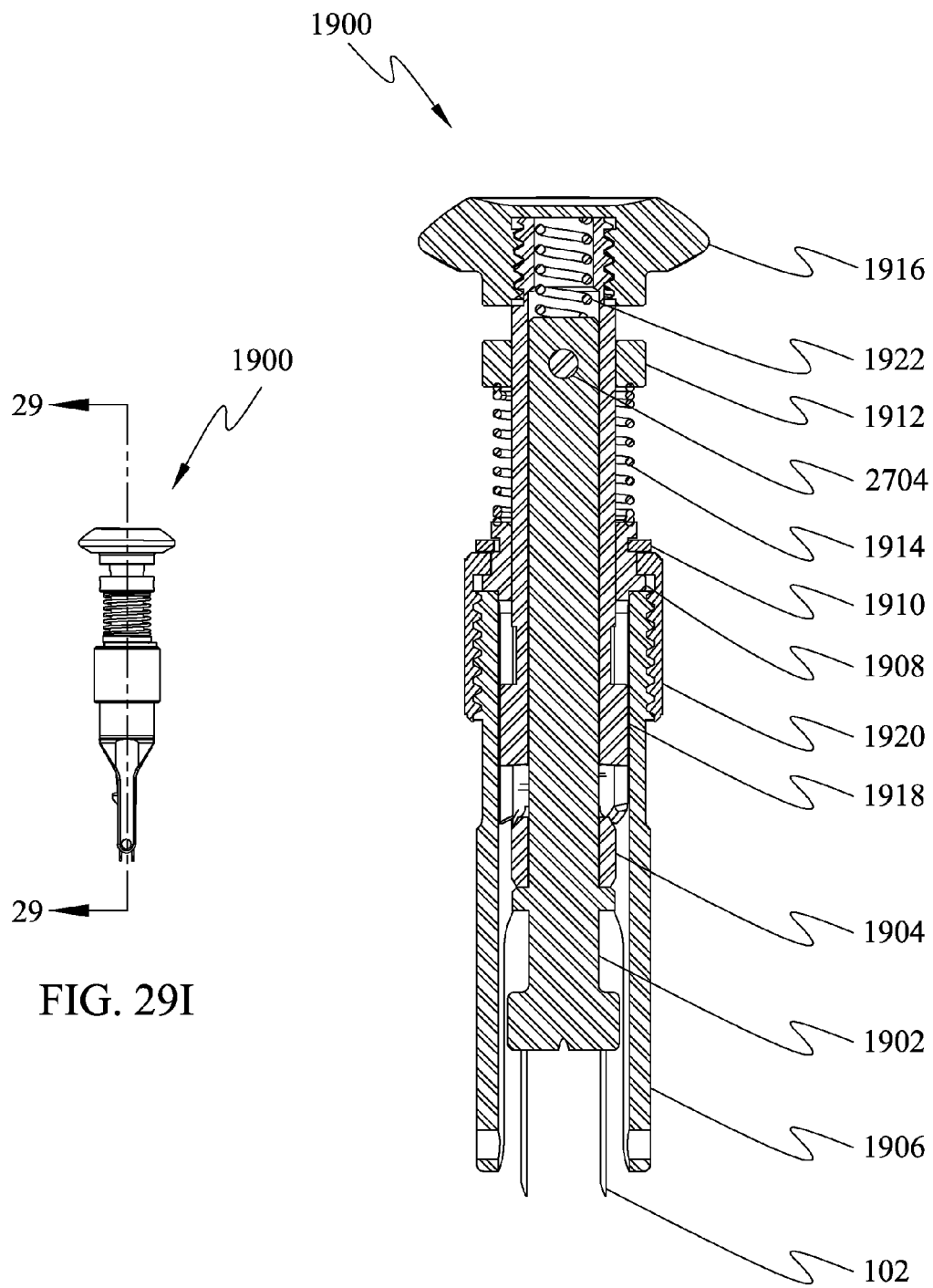
FIG. 29I is a side view of the assembly of FIG. 19.
FIG. 29J is a sectional view of the assembly of FIG. 19 about the axis 29-29.
Figure 30A:
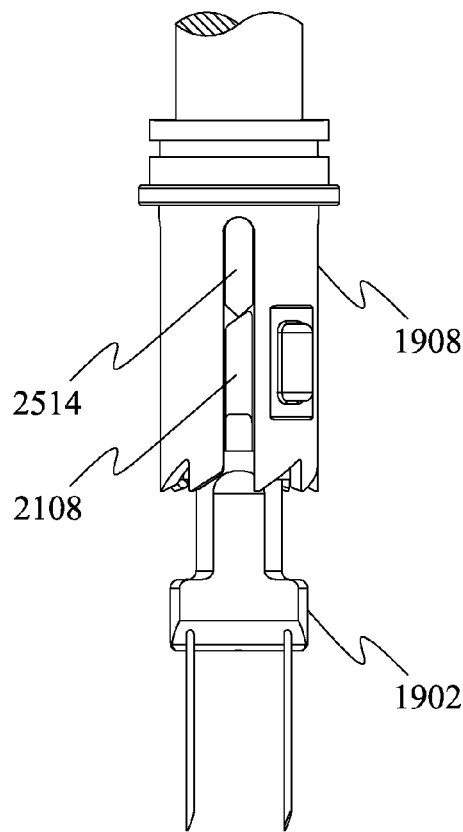
FIGS. 30A-30H are perspective views illustrating the working of the assembly of FIG. 19.
Figure 30B:
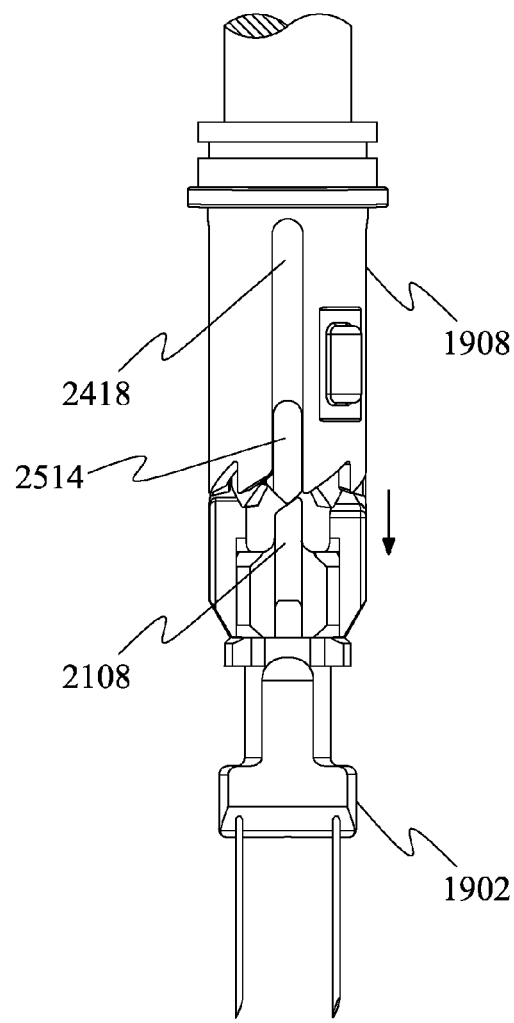
Figure 30C:
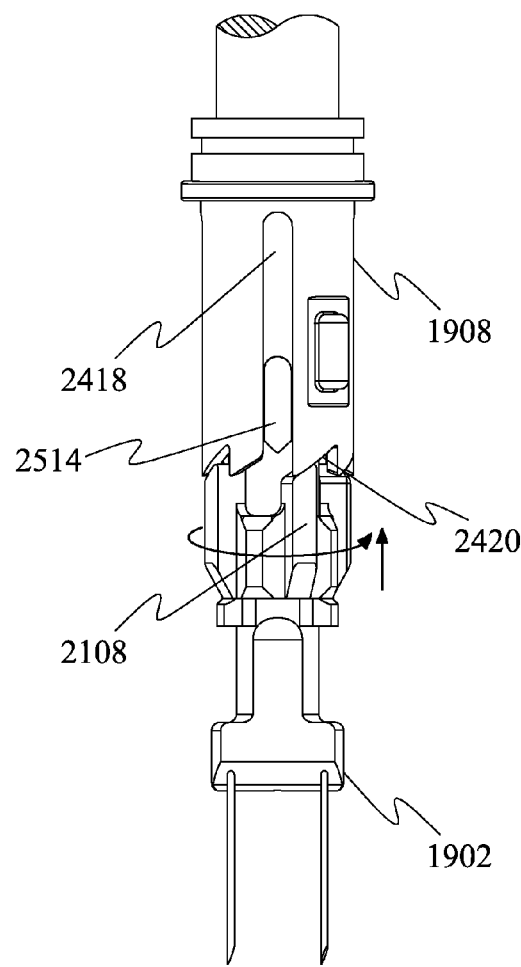
Figure 30D:
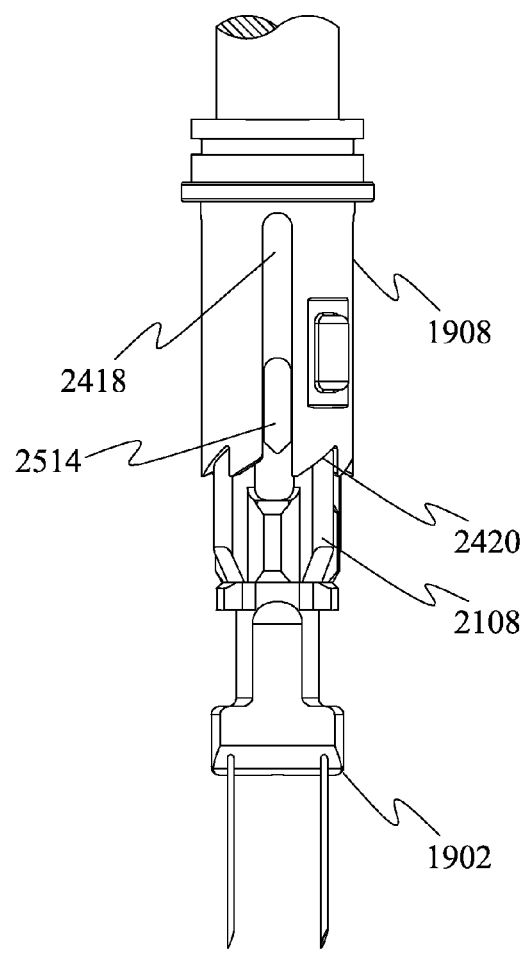
Figure 30E:
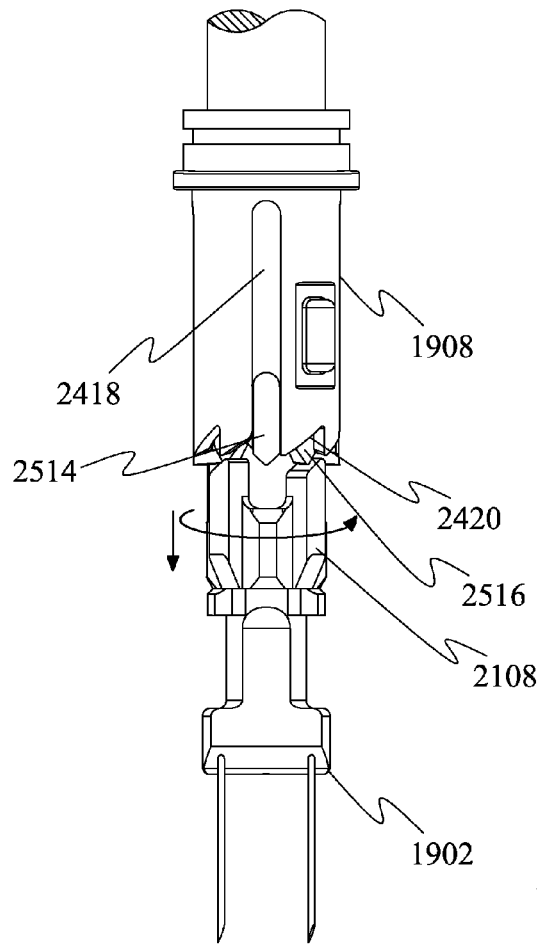
Figure 30F:
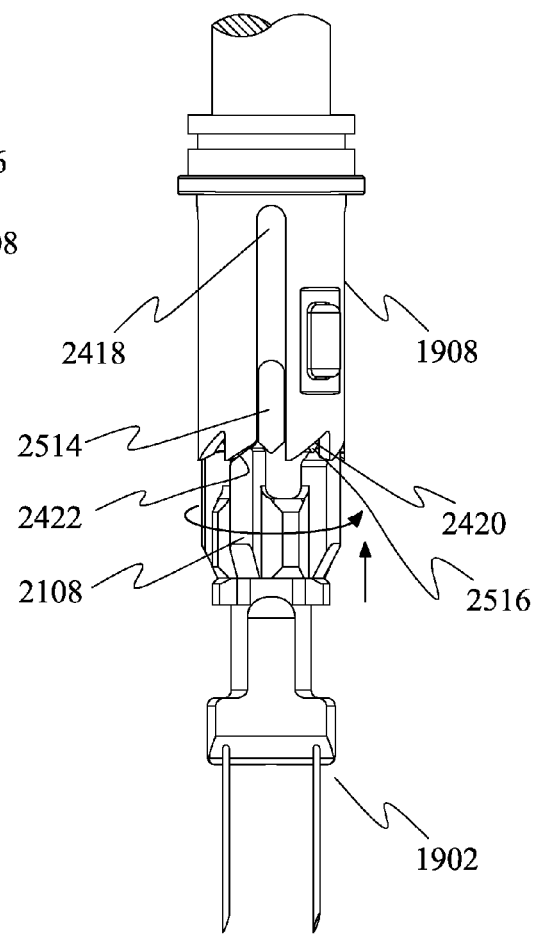
Figure 30G:
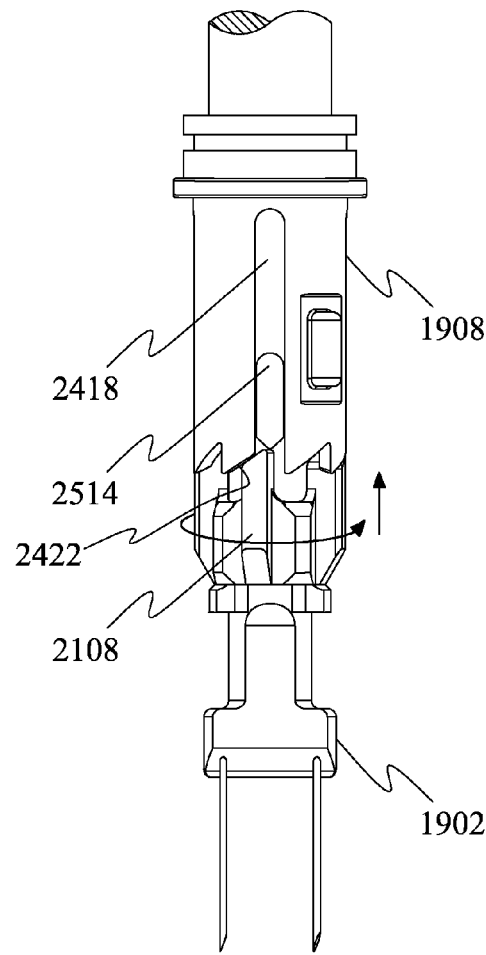
Figure 30H:
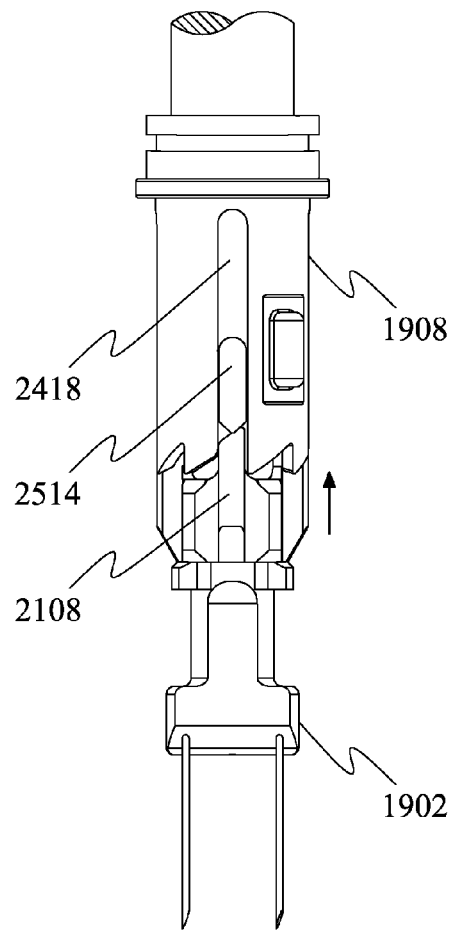

Referring to FIGS. 28A-28B, the knob 1920 may be operable to translate the shaft 1902 along a longitudinal axis of the shaft to configure the extent to which the piercing member 102 is extended into the external surface of the skin when the piercing member 102 is locked in the extended position. The engagement of the pivot enabling member 1906, second engagement member 1908 and the shaft 1902 with the knob 1920 may be such that the rotation of the knob 1920 may enable the shaft 1902 to partially translate in a first direction towards the external surface of the skin. Similarly the rotation of the knob 1920 in a direction opposite to the earlier direction may enable the shaft 1902 to partially translate in a second direction to move away from the external surface of the skin.

The knob 1920 may be rotated in a first direction. The rotation of the knob 1920 in the first direction may enable the knob 1920 to translate in a direction towards the cap 1916. The rotation of the knob 1920 in the first direction and the translatory motion of the knob 1920 in the may cause the compression member 1914 disposed over the knob 1920 to translate towards the cap 1916. The motion of the compression member 1914 may push the second ring 1912 towards the cap 1916. The second ring 1912, being engaged with the shaft 1902 through the pin 2704 may cause the shaft 1902 to move closer to the cap 1916, thereby decreasing the length, as indicated by arrow 2804, of the piercing members 102 that would be extended out of the assembly 1900 or into the skin, when the assembly 1900 is operated to lock the piercing members 102 in the extended position.

In order to increase the length, as indicated by arrow 2802, of the piercing members 102 that would be extended out of the assembly 1900 or into the skin, when the assembly 1900 is operated to lock the piercing members 102 in the extended position, the knob 1920 may be rotated in a second direction, opposite to the first direction. Rotation in the second direction may cause the knob 1920 to translate away from the cap 1916, allowing the second compression member 1922 to act on the shaft 1902, and push the shaft 1902 away from the cap 1916.

Referring to FIGS. 29A-29J, the shaft 1902 may be received through the engagement member 1904 such that the engagement member 1904 rests on top of the shoulder 2014. A portion of the shaft 1902 may be received by the indexer 1918 such that the through hole 2016 defined in the shaft 1902 and the through slot 2512 defined in the indexer 1918 may be aligned. The second engagement member 1908 may be received such that it encircles a portion of the indexer 1918. The pivot enabling member 1906 may be engaged with the second engagement member 1908, such that the pivot enabling member head 2608 may be pressed against the bottom of the shoulder 2410 of the second engagement member 1908. The first ring 1910 may be engaged around the second neck 2414 of the second engagement member 1908. The second ring 1912 may be disposed on top of the compression member 1914. The compression member 1914 may be placed below the second ring 1912 and on top of the head 2416 of the second engagement member 1908. The knob 1920 may be engaged around the pivot enabling member 1906. The neck 2508 of the indexer 1918 may be received by the threaded hole 2210 defined in the cap 1916. The neck 2508 of the indexer 1918 may be engaged with the cover portion 2208 and the lid portion 2206 of the cap 1916. The proximal end 2004 of the shaft 1902 may be received through the pivot enabling member 1906, the second engagement member 1908, the indexer 1918, the first ring 1910, the second ring 1912, and the compression member 1914. The second compression member 1922 may be disposed between the proximal end 2004 of the shaft 1902 and the lid portion 2206 of the cap 1916 and may be received by the indexer 1918.

Referring to FIGS. 30A-30H, the piercing members 102 may be made to pierce through an external surface of the skin, by pressing the cap 1916. Pressing of the cap 1916 may push the shaft 1902 towards the skin.

In the retracted position, the projection portions 2108 may be received in the retracted position lock slot 2418. Upon pressing the cap 1916, the first indexing tooth 2514 defined in the indexer 1918 may push the projection portions 2108 defined in the engagement member 1904. The engagement member 1904 moves downwards along the retracted position lock slot 2418. Once the projection portions 2108 moves out of the retracted position lock slot 2418, the projection portions 2108 begins to slide against the slanted surface of the first indexing tooth 2514, causing the engagement member 1904 to rotate. The engagement member 1904 which is being forced to move towards the cap 1916 by the compression member 1914, may begin to slid into the extended position lock slot 2420 and engage in the extended position lock slot 2420 to assume the extended position.

The retracted position may be assumed from the extended position by pressing the cap 1914. Pressing the cap 1916 may cause the second indexing tooth 2516 to push the projection portions 2108 thereby causing a partial rotation of the engagement member 1904. The engagement member 1904 may continue to rotate until it aligns with the rotation enabling surface 2422. The rotation enabling surface 2422 may further allow the engagement member 1904 to rotate further until the projection portions 2108 slides into the retracted position lock slot 2418. The engagement of the projection portions 2108 into the retracted position lock slot 2418 may stop further rotation of the engagement member 1904. The engagement member 1904 may now translate in the slot 2418 towards the cap 1914 to assume the retracted position.

The invention claimed is:

1. A system comprising,
    at least one piercing means for piercing through an external surface of a skin;
    a control means for locking the piercing means either in extended position or retracted position; and
    an alignment means for selecting:
        a first axis along which the piercing means translates to assume the extended position; and
        a second axis along which the piercing means translates to assume the retracted position, wherein the alignment means is operable to define an angle between the first axis and the second axis.

2. The system of claim 1, wherein the piercing means is configured to rotate about a rotational axis.

3. The system of claim 1, further comprising a targeting means for facilitating identification of a portion of the skin, wherein at least one hair follicle extends out of the skin at said portion of the skin, around which the piercing means pierce through the external surface of the skin.

4. The system of claim 1, further comprising a knob configured with the alignment means, wherein the knob is operable to translate the piercing means to configure the extent to which the piercing means is extended when the piercing member is locked in the extended position.

* * * * *